US00RE45587E

(19) United States
(12) Reissued Patent
Contorni et al.

(10) Patent Number: US RE45,587 E
(45) Date of Reissued Patent: Jun. 30, 2015

(54) VACCINES COMPRISING ALUMINUM ADJUVANTS AND HISTIDINE

(75) Inventors: Mario Contorni, Siena (IT); Massimo Maffei, Siena (IT)

(73) Assignee: GlaxoSmithKline Biologicals SA, Rixensart (BE)

(21) Appl. No.: 13/365,202

(22) Filed: Feb. 2, 2012

Related U.S. Patent Documents

Reissue of:
(64) Patent No.: 7,754,218
Issued: Jul. 13, 2010
Appl. No.: 11/968,920
Filed: Jan. 3, 2008

U.S. Applications:
(63) Continuation of application No. 10/484,702, filed as application No. PCT/IB02/03495 on Jul. 26, 2002, now Pat. No. 7,348,006.

(51) Int. Cl.
*A61K 39/02* (2006.01)
*A61K 39/38* (2006.01)
*A61K 39/116* (2006.01)
*C07K 14/00* (2006.01)
*A61K 38/00* (2006.01)

(52) U.S. Cl.
CPC ..... *A61K 38/00* (2013.01)

(58) Field of Classification Search
CPC ..... A61K 38/00
See application file for complete search history.

(56) References Cited

U.S. PATENT DOCUMENTS

| | | | | |
|---|---|---|---|---|
| 5,529,909 | A * | 6/1996 | della-Cioppa et al. | 435/69.7 |
| 6,472,518 | B1 | 10/2002 | Ribot et al. | |
| 7,348,006 | B2 * | 3/2008 | Contorni et al. | 424/184.1 |
| 7,576,176 | B1 | 8/2009 | Fraser et al. | |
| 7,785,608 | B2 | 8/2010 | Zlotnick et al. | |
| 7,862,827 | B2 | 1/2011 | Giuliani et al. | |
| 8,101,194 | B2 | 1/2012 | Zlotnick et al. | |
| 8,226,960 | B2 | 7/2012 | Masignani et al. | |
| 8,273,360 | B2 | 9/2012 | Pizza et al. | |
| 8,293,251 | B2 | 10/2012 | Scarlato et al. | |
| 8,394,390 | B2 | 3/2013 | Galeotti et al. | |
| 8,398,988 | B2 | 3/2013 | Contorni et al. | |
| 8,398,999 | B2 | 3/2013 | Masignani et al. | |
| 8,524,251 | B2 | 9/2013 | Fraser et al. | |
| 8,563,007 | B1 | 10/2013 | Zlotnick et al. | |
| 8,574,597 | B2 | 11/2013 | Zlotnick | |
| 8,734,812 | B1 | 5/2014 | Galeotti et al. | |
| 8,840,907 | B2 | 9/2014 | Pizza | |
| 2004/0092711 | A1 | 5/2004 | Arico | |
| 2004/0110670 | A1 | 6/2004 | Arico et al. | |
| 2004/0167068 | A1 | 8/2004 | Zlotnick et al. | |
| 2005/0106181 | A1 * | 5/2005 | Constantino | 424/238.1 |
| 2005/0222385 | A1 | 10/2005 | Pizza | |
| 2006/0051840 | A1 | 3/2006 | Arico et al. | |
| 2006/0171957 | A1 | 8/2006 | Pizza | |
| 2006/0240045 | A1 | 10/2006 | Berthet et al. | |
| 2006/0251670 | A1 | 11/2006 | Comanducci et al. | |
| 2007/0026021 | A1 | 2/2007 | Fraser et al. | |
| 2007/0082014 | A1 | 4/2007 | Costantino | |
| 2007/0253984 | A1 | 11/2007 | Khandke et al. | |
| 2008/0241180 | A1 | 10/2008 | Contorni | |
| 2009/0285845 | A1 | 11/2009 | Masignani et al. | |
| 2010/0267931 | A1 | 10/2010 | Arico et al. | |
| 2012/0107339 | A1 | 5/2012 | Granoff et al. | |
| 2014/0037668 | A1 | 2/2014 | Giuliani et al. | |

FOREIGN PATENT DOCUMENTS

| | | | |
|---|---|---|---|
| EP | 0467714 | | 1/1992 |
| EP | 0 835 663 | A2 | 4/1998 |
| EP | 0835663 | | 4/1998 |
| EP | 1645631 | A2 | 4/2006 |
| EP | 1790660 | A2 | 5/2007 |
| EP | 1409013 | B1 | 11/2009 |
| EP | 2351767 | A2 | 8/2011 |
| WO | WO-90/06696 | | 6/1990 |
| WO | WO-96/29412 | A1 | 9/1996 |
| WO | WO-98/17805 | | 4/1998 |
| WO | WO 99/48525 | * | 9/1999 |
| WO | WO 99/48525 | A1 | 9/1999 |
| WO | WO-99/57280 | A | 11/1999 |
| WO | WO-00/22430 | A2 | 4/2000 |
| WO | WO-00/45841 | | 8/2000 |
| WO | WO-00/57906 | | 10/2000 |
| WO | WO 00/57906 | A1 | 10/2000 |
| WO | WO-00/66791 | | 11/2000 |
| WO | WO-01/31019 | | 5/2001 |

(Continued)

OTHER PUBLICATIONS

Singh et al. (2006). A preliminary evaluation of alternative adjuvants to alum using a range of established and new generation vaccine antigens. Vaccine. 24(10):1680-6.
"MENCEVAX ACWY," International datasheet version 2.1, (May 15, 2000), 4 pages.
"MeNZB®" Drug datasheet (Jun. 23, 2009), 3 pages.
1997-11-17-NM_shotgun.dbs and 1997-12-15-NM.dbs, located at <ftp://ftp.sanger.ac.uk/pub/pathogens/nm/old data/>.
Aderson et al. (2010). "Effectiveness of a bivalent factor H binding protein vaccine across *Neisseria meningitidis* serogroups," 17th International Pathogenic *Neisseria* Conference 2010, p. 196.
Ala'Aldeen et al. (2010) "Human antibody response to the meningococcal factor H binding protein (LP2086) during invasive disease, colonization and carriage," Vaccine 28:7667-75.
Ambrose et al. (2006). "Characterization of LP2086 expression in *Neisseria meningitidis*," 15th International Pathogenic *Neisseria* Conference 2006, p. 103.
Anderson et al. (2008). "Functional cross-reactive antibodies are elicited by a group B *Neisseria meningitidis* bivalent recombinant lipidated LP2086 vaccine in cynomolgusmacaques," 16th International Pathogenic *Neisseria* Conference (IPNC) P100, pp. 170-171.

(Continued)

*Primary Examiner* — Albert Navarro
(74) *Attorney, Agent, or Firm* — Morrison & Foerster LLP

(57) ABSTRACT

To improve the stability of vaccines comprising aluminum salt(s), the invention uses the amino acid histidine. This can improve pH stability and adjuvant adsorption and can reduce antigen hydrolysis. Histidine is preferably present during adsorption to the aluminum salt(s). The antigen in the vaccine may be a protein or a saccharide and is preferably from N. meningitidis.

100 Claims, 4 Drawing Sheets

(56) References Cited

FOREIGN PATENT DOCUMENTS

| | | | | |
|---|---|---|---|---|
| WO | WO-01/37863 | | | 5/2001 |
| WO | WO-01/41800 | | | 6/2001 |
| WO | WO 01/41800 | A2 | | 6/2001 |
| WO | WO-01/52885 | | | 7/2001 |
| WO | WO-01/64920 | A | | 9/2001 |
| WO | WO 01/64922 | | * | 9/2001 |
| WO | WO-03/009869 | A1 | | 2/2003 |
| WO | WO-03/020756 | A | | 3/2003 |
| WO | WO-03/063766 | | | 8/2003 |
| WO | WO-2004/032958 | A1 | | 4/2004 |
| WO | WO-2004/048404 | | | 6/2004 |
| WO | WO-2004/065603 | A2 | | 8/2004 |
| WO | WO-2004/094596 | A2 | | 11/2004 |
| WO | WO-2006/024954 | A2 | | 3/2006 |
| WO | WO-2006/081259 | | | 8/2006 |
| WO | WO-2007/060548 | A2 | | 5/2007 |
| WO | WO-2007/127665 | A2 | | 11/2007 |
| WO | WO-2008/125985 | A2 | | 10/2008 |
| WO | WO-2008/149238 | A2 | | 12/2008 |
| WO | WO-2009/104097 | A2 | | 8/2009 |
| WO | WO-2010/028859 | A1 | | 3/2010 |
| WO | WO-2010/046715 | A1 | | 4/2010 |
| WO | WO-2010/109323 | A1 | | 9/2010 |

OTHER PUBLICATIONS

Anderson et al. (2009). "Development of a factor H binding protein vaccine for borad protection against invasive *Neisseria meningitidis* serogroup B (MnB) disease," 10th European Meningococcal Disease Society Congress 2009, p. 39.

Anderson et al. (2009). "Epidemiology of the serogroup B *Neisseria meningitidis* (MnB) factor H binding protein and implications for vaccine development," European Society for Paediatric Infectious Disease Symposium 2009, p. 505.

Anderson et al. (2012). "Potential impact of the bivalent rLP2086 vaccine on *Neisseria meningitidis* invasive disease and carriage isolates in two adolescent populations," European Society for Paediatric Infectious Disease Symposium 2012, p. 807.

Anderson et al. (2013) "Potential impact of the bivalent rLP2086 vaccine on *Neisseria meningitidis* carriage and invasive serogroup B disease," Hum Vacc Immunotherap 9:471-9.

Appendix I to Statement of Grounds of Appeal filed by df-mp on Sep. 28, 2012, in relation to EP164631, 1 pages.

Appendix II to Statement of Grounds of Appeal filed by df-mp on Sep. 28, 2012, in relation to EP1645631, 2 pages.

Aventis Pasteur (Feb. 2001). "MENOMUNE®—A/C/Y/W-135," Drug datasheet, 5 pages.

Beernick (Jul. 2010) "Impaired immunogenicity of a meningococcal factor H-binding protein vaccine engineered to eliminate factor h binding," Clin Vac Immunol 17(7):1074-1078.

Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.

Beernink et al. (Jun. 2008). "Bactericidal antibody responses, induced by meningococcal recombinant chimeric factor H-binding protein vaccines," Infection And Immunity 76(6):2568-2575.

Beernink et al. (Sep. 2008). "Fine antigenic specificity and cooperative bactericidal activity of monoclonal antibodies directed at the meningococcal vaccine candidate factor h-binding protein," Infection And Immunity 76(9):4232-4240.

BenMohamed et al. (2002). "Lipopeptide vaccines—yesterday, today, and tomorrow," Lancet 2(7):425-431.

Bentley et al. (2004). Identification of two immunologically distinct domains on the LP2086 outer membrane lipoprotein of *Neisseria meningitidis*, 14th International Pathogenic *Neisseria* Conference 2004, p. 144.

Bernfield L. et al. (Sep. 2002). "Identification of a novel vaccine candidate for group B *Neisseria meningitidis*," Thirteenth International Pathogenic *Neisseria* Conference, Norwegian Institute of Public Health, Oslo, Norway, pp. 116 and 124.

Beuvery et al. (1983). "Preparation and Immunochemical characterization of meningococcal group C polysaccharide-tetanus toxoid conjugates as a new generation of vaccines," Infect Immun 40:39-45.

Boslego et al. (1991). "Gonorrhea Vaccines," Chapter 17 In *Vaccines and Immunotherapy*, Cryz S.J. (Ed.), Pergamon Press: New York, NY, pp. 211-223.

Bouvier et al. (1991). "A gene for a new lipoprotein in the dapA-purC interval of the *Escherichia coli* chromosome," J Bacteriol 173(17):5523-5531.

Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2 (Suppl.):S1-S4.

Cantini et al. (Mar. 2006). "Solution Structure of the Immunodominant Domain of Protective Antigen GNA 1870 of *Neisseria meningitidis," Journal of Biological Chemistry* 281(11):7220-7227.

Chen, et al. (1994). "Determination of the optimal aligned spacing between the Shine-Dalgarno sequence and the translation initiation codon of *Escherichia coli* mRNAs," Nucleic Acids Res. 22(23):4953-4957.

Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.

Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1>.

Cohn et al. (2010). "Potential Impact of Serogroup B Vaccines: Prevalence of candidate vaccine antigens among invasive *Neisseria meningitidis* isolates in the United States," 17th International Pathogenic *Neisseria* Conference 2010, p. 77.

Cordis, "Preparation of meningococcal antigens," posted online on Feb. 2, 2005, 2 pages.

Cruse et al. (2003). Illustrated Dictionary of Immunology, 2nd Ed. CRC Press, pp. 46, 166, and 382.

Database accession No. NMB1994 (cf. XP2231040) (Tettelin et al.), uploaded Oct. 1, 2000.

Declaration by Dr. Ellen Murphy, Ph.D., dated Sep. 14, 2011, submitted in opposition proceedings for EP1645631, 4 pages.

Declaration by Dr. Julian Parkhill dated Jun. 12, 2008, submitted in opposition proceedings for EP1645631, 2 pages.

Declaration by E. Richard Moxon dated Feb. 16, 2013, submitted in opposition proceedings for EP1645631, 5 pages.

Declaration by Emilio A. Emini, Ph.D., dated Nov. 2, 2011, submitted in opposition proceedings for EP1645631, 5 pages.

Declaration by Isabel Delany, dated Feb. 18, 2013, submitted in opposition proceedings for EP1645631, 5 pages.

Declaration by Prof. Paul Dunman, Ph.D., dated Sep. 25, 2012, submitted in opposition proceedings for EP1645631, 14 pages.

Declaration by Rino Rappuoli, dated Oct. 13, 2011, submitted in opposition proceedings for EP1645631, 5 pages.

Declaration by Vega Masignani dated Feb. 18, 2013, submitted in opposition proceedings for EP1645631, 4 pages.

Declaration of Dr. Campanella dated Nov. 10, 2011, submitted in Opposition proceedings related to EP 1409013, 10 pages.

Declaration of Dr. Khandke dated Dec. 21, 2011, submitted in Opposition proceedings related to EP 1409013, 10 pages.

Delgado et al. (2007). "Lipoprotein NMB0928 from *Neisseria meningitidis* serogroup B as a novel vaccine candidate," Vaccine 25:8420-8431.

Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.

Dlawer et al. (2010). "Human antibody responses to the meningococcal factor H binding protein LP2086 during invasive disease," 17th International Pathogenic *Neisseria* Conference 2010, p. 130.

Facts and Submissions dated May 21, 2012, in relation to EP1645631, 30 pages.

(56) References Cited

OTHER PUBLICATIONS

Farley J. et al. (Sep. 2002). "Characterization, cloning and expression of different subfamilies of the ORF 2086 gene from *Neisseria meningitidis*," Thirteenth International Pathogenic *Neisseria* Conference, Norwegian Insitute of Public Health, Oslo, Norway, p. 124.
Feavers et al. (2009). "Meningococcal protein antigens and vaccines," Vaccine 275:B42-B50.
Fleischmann et al. (1995) "Whole-Genome Random Sequencing and Assembly of Haemophilus influenzae Rd," Science 269:496-501.
Fletcher et al. (2004). "Vaccine Potential of the *Neisseria meningitidis* 2086 Lipoprotein," *Infection and Immunity* 72(4): 2088-2100.
Fontana et al. (2002). A genomic approach Abstract from the 13$^{th}$ International Pathogenic *Neisseria* Conference, Oslo, Norway, Sep. 1-6, 2002. p. 248.
Fraser et al. (1997). "Genomic sequence of a lyme disease spirochaete, *Borrelia burgdorferi*," Nature 390:580-586.
Fraser et al. (1998). "Complete genome sequence of *Treponema pallidum*, the syphilis spirochete," Science 281:375-388.
GenPept accession No. AAF42204, "Hypothetical protein NMB1870 [*Neisseria meningitidis* MC58]," retrieved on Sep. 26, 2012, 2 pages.
Giuliani et al. (2006). "A universal vaccine for serogroup B meningococcus," PNAS 103(29):10834-10839.
Giuliani et al. (2010). "Measuring antigen-specific bactericidial responses to a multicomponent vaccine against serogroup B meningococcus," Vaccine 28:5023-5030.
Giuliani et al. (Feb. 2005). "The Region Comprising Amino Acids 100 to 255 of *Neisseria meningitidis* Lipoprotein GNA 1870 Elicits Bactericidal Antibodies," *Infection and Immunity* 73(2): 1151-1160.
Gold and Stormo (1987). "Translation Initiation", in *Escherichia* con and *Salmonella typhimurium*, Cellular and Molecular Biology, Ed. Neidhardt, pp. 1302-1307.
Gorringe et al. (2009). "16th International Pathogenic *Neisseria* Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27(Supplement 2): B117-B125.
Gupta (1998) "Aluminum compounds as vaccine adjuvants," Adv Drug Del Rev 32:155-172.
Harris et al. (2008). "Development and qualification of serum bactericidal assays for *Neisseria meningitidis* serogroup B," 16th International Pathogenic *Neisseria* Conference 2008, p. 268-269.
Harris et al. (2010). "Robustness of the Serum Bactericidal Activity (SBA) Assay for *Neisseria meningitidis* serogroup B," 17th International Pathogenic *Neisseria* Conference 2010, p. 169.
Harris et al. (2011) "Preclinical evidence for the potential of a bivalent fHBP vaccine to prevent *Neisseria meningitidis* serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic *Neisseria* Conference 2006, p. 113.
Hoiseth et al. (2008). "LP2086 and MLST distribution in epidemiologically relevant strains of serogroup B *Neisseria meningitidis*," 16th International Pathogenic *Neisseria* Conference 2008, p. 205.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The *Neisseria meningitidis* macrophage infectivity potentiator protein induces cross-strain serum bactericidal sctivity and is a potential serogroup B vaccine candidate," Infect Immun 79(9):3784-3791.
Jacobsson et al. (2009). "Prevalence and sequence variations of the genes encoding the five antigens includes in the novel 5CVMB vaccine covering group B meningococcal disease" Vaccine. 27:1579-1584.
Jansen et al. (2008). "Bivalent recombinant LP2086 vaccine to provide broad protection against *Neisseria meningitidis* B disease: immunological correlates of protection and how to assess coverage against invasive MnB strains," 16th International Pathogenic *Neisseria* Conference 2008, p. 80-81.
Jansen et al. (2009). "Development of a bivalent factor H binding protein vaccine to broadly protect against invasive *Neisseria meningitides* serogroup B (MnB) disease," European Society for Paediatric Infectious Disease Symposium 2009, p. 311.
Jansen et al. (2010). "Estimating effectiveness for *Neisseria meningitidis* serogroup B (MnB) vaccine candidates composed of non-serogroup specific antigens," 17th International Pathogenic *Neisseria* Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
JCVI-CMR website showing Z2491 Sanger sequence (http://cmr.jcvi.org/tigr-scripts/CMR/shared/Genomes.cgi and links). (2010).
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B *Neisseria meningitidis*," 15th International Pathogenic *Neisseria* Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic *Neisseria* Conference 2008, p. 57-58.
Jiang et al., (2010) "Broad vaccine coverage predicted for a bivalent recombinant factor H binding protein based vaccine to serogroup B meningococcal disease" Vaccine 28:6086-6093.
Johnson et al. (1999). "Analysis of the human Ig isotype response to lactoferrin binding protein A from *Neisseria meningitidis*," FEMS Immun. Med. Microbial. 25(4): 349-354.
Jones et al. (2009). "Generation of human serum complement lots that perform consistently for use in *Neisseria meningitidis* serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2007). "Improved immunogenicity of a H44/76 group B outer membrane vesicle vaccine with over-expressed genome-derived Neisserial antigen 1870," Vaccine 25(10):1912-1920.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Liebl et al. (1997). "Properties and gene structure of the Thermotoga maritima alpha-amylase AmyA, a putative lipoprotein of a hyperthermophilic bacterium," J Bacteriol 179(3):941-948.
Lucidarme et al., (Sep. 16, 2009) "Characterization of fHbp, nhba (gna2132)m, nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Marshall et al. (2008). "A randomized, placebo-controlled, double-blind, phase 1 trial of ascending doses of meningococcal group B

(56) References Cited

OTHER PUBLICATIONS rLP2086 vaccine in healthy adults," 16th International Pathogenic *Neisseria* Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic *Neisseria* Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
Masignani V. (Mar. 17, 2003). "Vaccination against *Neisseria meningitidis* using three variants of the lipoprotein GNA1870," J. Exp. Med. 197(6):789-799.
McNeil et al. (2009) "Detection of LP2086 on the cell surface of *Neisseria meningitidis* and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic *Neisseria* Conference 2010, p. 94.
McNeil et al. (2013) "Role of factor H binding protein in *Neisseria meningitidis* virulence and its potential as a vaccine candidate to broadly protect against meningococcal disease," Microbiol Mol Biol Rev 77:234.
Milagres et al. (1998). "Specificity of bactericidal antibody response to serogroup B meningococcal strains in Brazilian children after immunization with an outer membrane vaccine," Infection and Immun. 66(10): 4755-4781.
Morley, S. et al. (Dec. 12, 2001). "Vaccine prevention of meningococcal disease, coming soon?" *Vaccine* 20(5-6):666-687.
Munkley, et al. (1991). "Blocking of bactericidal killing of *Neisseria meningitidis* by antibodies directed against slacc 4 outer membrane proteins," Microbial Pathogenesis 11: 447-452.
Murphy et al. (2008). "Sequence diversity of vaccine candidate LP2086 in *Neisseria meningitidis* serogroup B strains causing invasive disease," 16th International Pathogenic *Neisseria* Conference 2008, p. 61.
Murphy et al. (2010). "Prevalence of Factor H Binding Protein (fHBP) Variants in *N. meningitidis* Carriage Isolates," 17th International Pathogenic *Neisseria* Conference 2010, p. 96.
Murphy et al., (2009) "Sequence diversity of the factor H binding protein vaccine candidate in epidemiologically relevant strains of serogroup B *Neisseria meningitidis*" J Infect Dis 200:379-389.
Nassif (2000). "A Furtive Pathogen Revealed," Science 287:1767-1768.
Notice of Opposition against European Patent EP 1645631, granted on Oct. 24, 2007. Opposition filed on Jul. 23, 2008. 20 pages.
Novartis (Jan. 22, 2013) "Novartis receives EU approval for Bexsero®, first vaccine to prevent the leading cause of life-threatening meningitis across Europe," Media Release, 3 pages.
Novartis (Oct. 9, 2008) "New Phase II data show Novartis investigational Meningitis B vaccine may also protect infants six months and older," Media Release, 4 pages.
Pajon et al. (2010). "Frequency of factor H-binding protein modular groups and susceptibility to cross-reactive bactericidal activity in invasive meningococcal isolates" Vaccine 28:2122-2129.
Pajon et al. (2012). "Design of meningococcal factor H binding protein mutant vaccines that do not bind human complement factor H," Infect Immun 80:2667-2677.
Parkhill, "*Campylobacter jejuni* genome sequence at the Sanger Centre," Post on BIOSCI/Bionet of May 8, 1998.
Parkhill, J. et al. (Mar. 2000). "Complete DNA Sequence of a Serogroup A Strain of *Neisseria* meningitides Z2491," *Nature* 404(6777):502-506.
Patentees' Response to Opposition against European Patent EP 1645631, granted on Oct. 24, 2007. 13 pages.
Pettersson, et al. (2006). "Vaccine potential of the *Neisseria meningitidis* lactoferrin-binding proteins LbpA LbpB," Vaccine 24(17):3545-3557.
Pillai et al. (2005) "Outer membrane protein (OMP) based vaccine for *Neisseria meningitidis* serogroup B," Vaccine 23(17-18):2206-2209.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161.5. Oct. 28, 2009.
Richmond et al. (2008). "A randomized, observer-blinded, active control, phase 1 trial of meningococcal serogroup B rLP2086 vaccine in healthy children and adolescents aged 8 to 14 years," 16th International Pathogenic *Neisseria* Conference 2008, p. 270-271.
Richmond et al. (2010). "Safety & immunogenicity of serogroup B *Neisseria meningitidis* (MnB) rLP2086 vaccine in adults and adolescent subjects: overview of 3 clinical trials," 17th International Pathogenic *Neisseria* Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent *Neisseria meningitidis* recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rinaudo et al. (2009). "Vaccinology in the genome era", The Journal of Clinical Investigation, 119(9):2515-2525.
Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of *Neisseria* meningitides," Journal of Molecular Biology 386(1):97-108.
Schneider et al. (Apr. 16, 2009) "*Neisseria meningitidis* recruits factor H using protein mimicry of host carbohydrates," Nature 458(7240):890-893.
Seeber et al. (1991). "Predicting the adsorption of proteins by aluminum-containing adjuvants," Vaccine 9(3):201-203.

(56) References Cited

OTHER PUBLICATIONS

Seib et al. (2010). "Influence of serogroup B meningococcal vaccine antigens on growth and survival of the mengococcus in vitro and in ex vivo and in vivo models of infection," Vaccine 28(12):2416-2427.
Sepelyak et al. (1984). "Adsorption of pepsin by aluminum hydroxide I: adsorption mechanism," J Pharm Sci 73:1514-17.
Sequence for "Putative Lipoprotein [*Neisseria meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Sheldon et al. (2011). "Phase 1, Randomized, Open-Label, Study to Assess the Safety and Immunogenicity of Serogroup B *Neisseria meningitidis* (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of *Erwinia chrysanthemi* 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Ressell (1995). "Lipoproteins of gram-positive bacteria," J Bacteriol 177(5):1123-1128.
Tan et al. (2010). "Advances in the development of vaccines against *Neisseria meningitidis*," NEJM 362(16):1511-1520.
Telford et al. (2003). "Genomic and Proteomics in Vaccine Design", in *New Bacterial Vaccines*, edited by Ellis et al. Kleweur Academic/ Plenum Publishers, USA. pp. 1-11.
Tettelin et al. (Mar. 10, 2000). "Complete Genome Sequence of *Neisseria meningitidis* Serogroup B Strain MC58," Science 287(5459):1809-1815.
The printed output from the NCBI open reading frame finder (Oct. 20, 2008), 12 pages.
TIGR website as of 1998, 8 pages.
United States Office Action mailed of Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence And Uses Thereof," filed Sep. 1, 1998.
von Heijne (1989). "The structure of signal peptides from bacterial lipoproteins," Protein Engineering 2(7):531-534.
Wang et al. (2010). "Prevalence and genetic diversity of candidate vaccine antigens among invasive *Neisseria meningitidis* isolates in the United States," 17th International Pathogenic *Neisseria* Conference 2010, p. 122.
Welsch et al. (2004). "Protective Activity of Monclonal Antibodies to Genome-Derived Neisserial Antigen 1870, a *Neisseria meningitidis* Candidate Vaccine," *The Journal of Immunology* 172: 5606-5615.
Welsch et al. (2007) "A novel mechanism for complement-mediated killing of encapsulated *Neisseria meningitidis* elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monocolonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic *Neisseria* Conference 2010, p. 109.
Zhu et al. (2004). "Evaluation of the purified recombinant lipidated P2086 protein as a vaccine candidate for group B *Neisseria meningitidis* in a murine nasal challenge model," 14th International Pathogenic *Neisseria* Conference 2004, p. 199.
Zhu et al. (2005) "Evaluation of recombinant lipidated P2086 protein as a vaccine candidate for group B *Neisseria meningitidis* in a murine nasal challenge model," Infect Immun 73(10):6838-45.
Zhu et al. (2006) "Intranasal immunization of mice with recombinant lipidated P2086 protein reduces nasal colonization of group B *Neisseria meningitidis*," Vaccine 24:5420-5.
Zhu et al. (2006). "Effective immunization strategy against group B *Neisseria meningitidis* using purified recombinant lipidated P2086 protein," 15th International Pathogenic *Neisseria* Conference 2006, p. 47.
Zlotnick et al. (2009). "Epidemiology of the serogroup B *Neisseria meningitidis* (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of *N. meningitidis*," 17th International Pathogenic *Neisseria* Conference 2010, p. 38.
Database UniProt (Oct. 1, 2000), "SubName: Full=Uncharacterized protein" retrieved from EBI, accession No. Q9JXV4 Database accession No. Q9JXV4.
Decision revoking the European Patent, filed in opposition against EP1976990, dated Nov. 11, 2013, 15 pages.
Donnelly et al. (2010). "Qualitative and quantitative assessment of meningococcal antigens to evaluate the potential strain coverage of protein-based vaccines," Proc Natl Acad Sci U S A, 107(45):19490-5.
Experimental data: expression of NspA, '287' and '741' on 3 strains of bacteria, filed in opposition against EP1534326, dated Aug. 4, 2010. 2 pages.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Kovacs-Simon et al. (2011). "Lipoproteins of Bacterial Pathogens," Infect Immun 79(2):548-561.
Lewis et al. (2010). "The meningococcal vaccine candidate neisserial surface protein A (NspA) binds to factor H and enhances meningococcal resistance to complement," PLoS Pathogens 6(7):e1001027.
Liechti et al. (2012). "Outer membrane biogenesis in *Escherichia coli, Neisseria meningitidis*, and *Helicobacter pylori*: paradigm deviations in *H. pylori*," Front Cell and Infect Microbiol 2:article 29.
Lindblad, (2004). "Aluminium compounds for use in vaccines," Immunol Cell Biol.,82(5):497-505.
Madico et al. (2006). "The meningococcal vaccine candidate GNA1870 binds the complement regulatory protein factor H and enhances serum resistance," J Immunol 177(1):501-510.
Notice of Opposition filed May 24, 2012, filed in opposition against EP1976990, 19 pages.
Novartis (Jun. 9, 2011). "Novartis candidate vaccine Bexsero® shows significant potential in providing broad coverage against meningococcal serogroup B infections." Media Release, 6 pages.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.

(56) References Cited

OTHER PUBLICATIONS

Sandbu et al. (2007). "Immunogenicity and safety of a combination of two serogroup B meningococcal outer membrane vesicle vaccines," Clin Vaccine Immunol, 14(9):1062-9.
Seib et al. (2011). "Characterization of Diverse Subvariants of the Meningococcal Factor H (fH) Binding Protein for Their Ability To Bind fH, To Mediate Serum Resistance, and To Induce Bactericidal Antibodies," Infect Immun, 79(2):970-81.
U.S. Appl. No. 60/647,911, "GNA 1870-based vesicle vaccines for broad spectrum protection against diseases caused by *Neisseria meningitidis*," filed Jan. 27, 2005.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
Voulhoux and Tommassen (2002). "Transport of lipoproteins to the cell surface in *Neisseria meningitidis*," 13th International Pathogenic *Neisseria* Conference 2002, p. 31.
Written Submission to Oral Proceedings, filed in opposition against EP1976990, dated Jul. 24, 2013, 11 pages.
Zollinger et al. (2010). "Design and evaluation in mice of a broadly protective meningococcal group B native outer membrane vesicle vaccine," Vaccine, 28(31):5057-5067.
Adams (1996). "Should Non-Peer-Reviewed Raw DNA Sequence Data Release Be Forced on the Scientific Community?," Science, 274: 534-536.
Biswas et al. (1995). "Characterization of IbpA, the structural gene for a lactoferrin receptor in *Neisseria gonorrhoeae*," Infection and Immunity, 63(8): 2958-2967.
Blattner et al. (1997). "The complete genome sequence of *Escherichia coli* K-12," Science 277 (5331):1453-1474.
Decision to refuse a patent application, filed in the Opposition against EP1645631, dated Apr. 28, 2009, 7 pages.
Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Elzanowski et al. (2013). "The Genetic Codes, a compilation," Retrived from http://www.bioinformatics.org/JaMBW/2/3/TranslationTables.html.
Holst et al. (2014). "Variability of genes encoding surface proteins used as vaccine antigens in meningococcal endemic and epidemic strain panels from Norway," Vaccine 32:2722-2731.
Mahadevan (1998). "Reconciling the spectrum of Sagittarius A* with a two-temperature plasma model," Nature 394:651-653.
Meyer et al. (1984). "Pilus genes of *Neisseria gonorrheae*: Chromosomal organization and DNA sequence," Proc. Nail. Acad. Sci. USA 81: 6110-6114.
Minutes of the oral proceedings, filed in the Opposition against EP1645631, dated Feb. 11, 2014, 4 pages.
Opponent's Response to the Patentee's Submission dated Feb. 18, 2013, filed in the Opposition against EP1645631, dated Jul. 24, 2014, 34 pages.
ORF Finder (2013). "Bacterial Code," Retrieved from http://www.ncbi.nlm.nih.gov/gorf/gorf.html, 3 pages.
Sprengart et al. (1997). "Functional importance of RNA interactions in selection of translation initiation codons," Molecular Microbilogy, 24(1): 19-28.
Summons to oral proceedings pursuant to Rule 115(1) EPC, filed in the Opposition against EP1645631, dated Nov. 11, 2013, 12 pages.
Swaminathan (1996). "Molecular cloning of the three base restriction endonuclease R.CviJI from eukaryotic Chlorella virus IL-3A. Swaminathan," Nucleic Acids Research, 24(13): 2463-2469.
Gene Browser, Nature Technology Corporation, filed in the Opposition against EP1645631, dated Jun. 26, 2013, 6 pages.
TIGR Microbal Database, filed in the Opposition against EP1645631, dated Jun. 20, 2012, 14 pages.
Submission of the Patentee of Jul. 6, 2012, filed Jun. 24, 2014, in the Opposition against EP1645631, 4 pages.
Notice of Opposition against EP 1409013, dated Aug. 18, 2010. 22 pages.
Patentee's Response to Opposition (EP 1409013), dated Apr. 7, 2011. 13 pages.
Opponent's Observations under Rule 116 EPC Prior to Oral Proceedings, filed in Opposition against EP 1409013, dated Nov. 17, 2011. 12 pages.
Patentee's Pre-Hearing Submissions Under Rule 116 EPC, filed in Opposition against EP 1409013, dated Nov. 17, 2011. 12 pages.
Response to the Proprietor's Submission of Nov. 17, 2011, filed in Opposition against EP 1409013, dated Dec. 21, 2011. 12 pages.
Decision revoking EP 1409013, dated Mar. 8, 2012, 12 pages.
Patentee's statement of grounds in support of its appeal, filed in Opposition against EP 1409013, Jul. 18, 2012, 5 pages.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Patentee's Submissions under Rule 116 EPC, filed in the Opposition against EP1645631, dated Sep. 13, 2011, 13 pages.
Opponents Final Written Submission in Preparation of Oral Proceedings, filed in the Opposition against EP1645631, dated Sep. 14, 2011, 28 pages.
Opponent's Further Submission in Preparation of the Oral Proceedings, filed in the Opposition against EP1645631, dated Nov. 3, 2011, 6 pages.
Supplementary Submission to the Grounds of Appeal, filed in the Opposition against EP1645631, dated Sep. 28, 2012, 2 pages.
Interlocutory decision in opposition proceedings, filed in the Opposition against EP1645631, dated May 21, 2012, 82 pages.
Ai Hommet, "Assessment of the Stability and Immunogenicity of Meningococcal Oligosaccharide C-CRM197 Conjugate Vaccines," Vaccine, Butterworth Scientific. Guildford, GB, vol. 19, No. 7-8, pp. 716-725, XP004225388, Nov. 22, 2000.

* cited by examiner

VACCINES COMPRISING ALUMINUM ADJUVANTS AND HISTIDINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*More than one reissue application has been filed for the reissue of U.S. Pat. No. 7,754,218. The reissue applications are application Ser. No. 14/020,607 (filed Sep. 6, 2013, which is a reissue divisional of this application Ser. No. 13/365,202) and application Ser. No. 13/365,202 (the present application, filed Feb. 2, 2012). This application is an application for reissue of U.S. Pat. No. 7,754,218.*

CROSS-REFERENCE TO RELATED APPLICATIONS

This application is a continuation of U.S. Application Ser. No. 10/484,702, filed Feb. 17, 2005, now U.S. Pat. No. 7,348,006, which is a national stage application under 35 U.S.C. §371 of International Application No. PCT/IB02/03495, filed Jul. 26, 2002, which claims the benefit of priority of British Application No. GB0118249.2, filed Jul. 26, 2001, and International Application No. PCT/IB02/03191, filed Jun. 20, 2002. Each of the above-referenced applications is hereby incorporated by reference in its entirety.

TECHNICAL FIELD

This invention is in the field of vaccine formulation.

BACKGROUND ART

As well as containing antigenic substances, vaccines contain substances such as diluents, excipients, preservatives, stabilisers and buffers. Typically, vaccines also contain adjuvants, i.e., a substance which improves the immune response raised in response to the vaccine antigen.

The adjuvants traditionally used in human vaccines have been aluminium salts such as aluminium hydroxide and aluminium phosphate. Many other experimental adjuvants are known and these are reviewed in, for instance, reference 1. Adsorption to aluminium salts remains, however, the most common vaccine adjuvant formulation.

Although their use is widespread, aluminium salts may not always be compatible with particular antigens. It has been suggested, for instance, that aluminium hydroxide may not be suitable for use in multivalent vaccines including hepatitis B virus surface antigen [2] or for use with the capsular polysaccharide from Haemophilus influenzae [3]. It has also been suggested that different antigens within the same vaccine formulation should be adsorbed to different aluminium salts [4] for compatibility reasons.

As well as antigen compatibility, it is necessary to consider vaccine stability when using aluminium salts. For instance, their capacity for protein adsorption has been shown to drop over time at room temperature [5] and in response to autoclaving [6]. Alum salts may also cause difficulties in freeze drying [7]. Furthermore, it has been found that aluminium hydroxide can hydrolyse saccharide antigens [8], even at low temperatures and when the antigen is conjugated to a carrier protein, thus leading to reduced efficacy.

In general, these issues only arise when attention moves to formulating an antigen for clinical use and may not be appreciated during initial research and development of the antigen itself.

It is an object of the invention to provide improvements in the stability of vaccines which include aluminium salts and, in particular, improvements in pH stability (buffering) and adjuvant adsorption at various temperatures and/or improvements in antigen stability (e.g., reduction in hydrolysis).

DISCLOSURE OF THE INVENTION

The invention is based on the surprising discovery that the amino acid histidine enhances the stability of vaccines which include aluminium salt adjuvants. This has been found both for saccharide antigens and for protein antigens.

The invention thus provides a composition comprising an antigen, an aluminium salt and histidine. The invention also provides a process for producing this composition, comprising the step of admixing an antigen, an aluminium salt and histidine.

The Antigen

The antigen is preferably a protein antigen or a saccharide antigen (optionally conjugated). Preferred antigens are from bacteria, with the bacterial genus Neisseia (e.g. N. meningitidis) being particularly preferred.

Specific bacterial antigens for use with the invention include:

- a protein antigen from N. meningitidis serogroup B, such as those in refs. 9 to 15, with protein '287' (see below) and derivatives (e.g. 'ΔG287') being particularly preferred,
- an outer-membrane vesicle (OMV) preparation from N. meningitidis serogroup B, such as those disclosed in refs. 16, 17, 18, 19 etc.
- a saccharide antigen from N. meningitidis serogroup A, C, W135 and/or Y, such as the oligosaccharide disclosed in ref 20 from serogroup C [see also ref. 21].
- a saccharide antigen from Streptococcus pneumoniae [e.g. 22, 23, 24].
- an antigen from Bordetella pertussis, such as pertussis holotoxin (PT) and filamentous haemagglutinin (FHA) from B. pertussis, optionally also in combination with pertactin and/or agglutinogens 2 and 3 [e.g. refs. 25 & 26].
- a diphtheria antigen, such as a diphtheria toxoid [e.g. chapter 3 of ref. 27] e.g. the $CRM_{197}$ mutant [e.g. 28].
- a tetanus antigen, such as a tetanus toxoid [e.g. chapter 4 of ref 27].
- a protein antigen from Helicobacter pylori such as CagA [e.g. 29], VacA [e.g. 29], NAP [e.g. 30], HopX [e.g. 31], HopY e.g. [31] and/or urease.
- a saccharide antigen from Haemophilus influenzae B [e.g. 21], preferably oligosaccharide.
- an antigen from N. gonorrhoeae [e.g. 9, 10, 11].
- an antigen from Chlamydia pneumoniae [e.g. 32, 33, 34, 35, 36, 37, 38].
- an antigen from Chlamydia trachomatis [e.g. 39].
- an antigen from Porphyromonas gingivalis [e.g. 40].
- an antigen from Moraxella catarrhalis [e.g. 41].
- an antigen from Streptococcus agalactiae (group B streptococcus) [e.g. 42, 43].
- an antigen from Streptococcus pyogenes (group A streptococcus) [e.g. 43, 44, 45].

an antigen from Staphylococcus aureus [e.g. 46].

an antigen from Bacillus anthracis [e.g. 47, 48, 49].

Specific viral antigens for use with the invention include:

an antigen from hepatitis A virus, such as inactivated virus [e.g. 50, 51].

an antigen from hepatitis B virus, such as the surface and/or core antigens [e.g. 51, 52].

an antigen from hepatitis C virus [e.g. 53].

polio antigen(s) [e.g. 54, 55] such as IPV.

rabies antigen(s) [e.g. 56] such as lyophilised inactivated virus [e.g. 57, RabAvert™].

measles, mumps and/or rubella antigens [e.g. chapters 9, 10 & 11 of ref. 27].

influenza antigen(s) [e.g. chapter 19 of ref. 27], such as the haemagglutinin and/or neuraminidase surface proteins.

an antigen from a virus in the flaviviridae family (genus flavivirus), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

The composition may comprise one or more of these bacterial and viral antigens The composition may comprise no viral antigens.

Other antigens which may be used include:

a prion protein (e.g. the CJD prion protein)

an amyloid protein, such as a beta peptide [58]

a cancer antigen, such as those listed in Table 1 of ref. 59 or in tables 3 & 4 of ref. 60.

Where a saccharide or carbohydrate antigen is used, it is preferably conjugated to a carrier protein in order to enhance immunogenicity [e.g. refs. 61 to 70]. Preferred carrier proteins are bacterial toxins or toxoids, such as diphtheria or tetanus toxoids. The $CRM_{197}$ diphtheria toxoid is particularly preferred. Other suitable carrier proteins include the N. meningitidis outer membrane protein [e.g. ref. 71], synthetic peptides [e.g. 72, 73], heat shock proteins [e.g. 74], pertussis proteins [e.g. 75, 76], protein D from H. influenzae [e.g. 77], toxin A or B from C. difficile [e.g. 78], etc. Where a mixture comprises capsular saccharides from both serogroups A and C, it is preferred that the ratio (w/w) of MenA saccharide: MenC saccharide is greater than 1 (e.g. 2:1, 3:1, 4:1, 5:1, 10:1 or higher). Saccharides from different serogroups of N. meningitidis may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or genetic means [26]).

Human papilloma virus (HPV) virus-like particles (VLPs) are not preferred antigens (cf. WO00/45841, WO00/57906, WO01/28585).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Whole cell pertussis antigen may be used.

Antigen is preferably adsorbed to the aluminium salt.

Where HBsAg is present, preferably it is either adsorbed to aluminium hydroxyphosphate or is not adsorbed to any salt. Adsorption of HBsAg to an aluminium hydroxide is preferably avoided.

Where a H. influenzae saccharide antigen is present, preferably it is either adsorbed to aluminium hydroxyphosphate or is not adsorbed to any salt. Adsorption of Hib saccharides to an aluminium hydroxide is preferably avoided.

Antigens in the composition will typically be present at a concentration of at least 1 μg/ml each. In general, the concentration of any given antigen will be sufficient to elicit an immune response against that antigen.

As an alternative to using proteins antigens in the composition of the invention, nucleic acid encoding the antigen may be used [e.g. refs. 79 to 87]. Protein components of the compositions of the invention may thus be replaced by nucleic acid (preferably DNA e.g. in the form of a plasmid) that encodes the protein.

The Aluminium Salt

The aluminium salt is preferably an aluminium hydroxide (e.g. aluminium oxyhydroxide) or an aluminium phosphate (e.g. aluminium hydroxyphosphate or orthophosphate), but any other suitable salt may also be used (e.g. sulphate etc. [e.g. see chapters 8 & 9 of ref. 1]). The salt may take any suitable form (e.g. gel, crystalline, amorphous etc.). Preferred salts are (amorphous) hydroxyphosphates and (crystalline) oxyhydroxide (boehmite).

Hydroxyphosphates are obtained by precipitation and the reaction conditions and reactant concentrations during the precipitation reaction influence the degree of substitution of phosphate for hydroxyl in the salt. Hydroxyphosphates generally have a $PO_4$/Al molar ratio between 0.3 and 0.99, and preferred salts have a ratio between 0.8 and 0.95 (e.g. 0.88±0.05). Hydroxyphosphates $[Al(OH)_x(PO_4)_y$, wherein the sum of the valence of each anion times its mole fraction is −3] can be distinguished from $AlPO_4$ by the presence of hydroxyl groups. For example, an IR spectrum band at 3146 $cm^{-1}$ (e.g. when heated to 200° C.) indicates the presence of structural hydroxyls.

Aluminium oxyhydroxide [AlO(OH)] can be distinguished from $Al(OH)_3$ by IR spectroscopy, in particular by the presence of an adsorption band at 1070 $cm^{-1}$ and a strong shoulder at 3090-3100 $cm^{-1}$, Mixtures of different aluminium salts may also be used. It is preferred, however, to use essentially a single salt e.g. where two salts are used, the ratio of one to the other is at least 5:1 by weight e.g. at least 10:1, 100:1, 1000:1 etc.

The salt will generally be present such that the concentration of $Al^{3+}$ is at least 1 μg/ml (e.g. at least 10 μg/ml, at least 100 μg/ml etc.).

The use of histidine in combination with an aluminium phosphate (particularly a hydroxyphosphate) is particularly advantageous for acidic antigens.

The Histidine

Histidine is a standard amino acid and is readily available for use with the invention. As it is inherently biocompatible, it is safe, and thus advantageous as an component in vaccines.

The concentration of histidine in the composition will typically be at least 1 μm and at most 1M. The concentration is preferably at least 1 mM (e.g. at least 2 mM, 3 mM, 4 mM, 5 mM etc.) and is preferably at most 250 mM (e.g. at most 20 mM, 150 mM, 100 mM, 90 mM, 80 mM, 70 mM, 60 mM, 50 mM, 40 mM, 30 mM, 20 mM, 10 mM etc.). More preferably the concentration of histidine in the composition is between 2 mM and 10 mM (e.g. between 5 mM and 8 mM) and, most preferably, it is about 5 mM.

The histidine is preferably L-histidine.

The histidine preferably acts as a buffer. Histidine buffers are well known to the skilled person. Accordingly, the histidine may be ionised within the composition of the invention.

The composition preferably has enhanced pH stability and/or reduced antigen hydrolysis when compared to an equivalent composition in which histidine buffer system is either replaced with a sodium phosphate buffer system or in which no buffer system is included Reduced hydrolysis may be a consequence of enhanced pH stability.

Histidine may be added to the composition in the form of the amino acid itself or in the form of a salt. A typical histidine salt is the monohydrochloride monohydrate.

It will be appreciated that references to histidine in the compositions of the invention refers to 'free' histidine rather than to any histidine residues which may be part of a polypeptide (e.g. the antigen) within the composition.

Further Characteristics of the Composition

The composition is preferably in liquid form, but it may be lyophilised (c WO01/41800).

The composition may also comprise a sodium salt e.g. sodium phosphate or sodium chloride. The concentration of the sodium salt is preferably at least 1 mM (e.g. at least 2 mM, 3 mM, 4 mM, 5 mM etc.) and is preferably at most 10 mM (e.g. at most 10 mM, 9 mM, 8 mM, 7 mM etc.). More preferably the concentration of sodium salt in the composition is between 1 mM and 5 mM (e.g. between 2 mM and 3 mM) and, most preferably, it is about 2.5 mM.

A particular advantage of the invention is that it allows good control of pH and adsorption in vaccines which contain high concentrations of free phosphate ions, which ions may be unavoidable in the vaccine e.g. due to exchange with phosphates in the adjuvant, or due to residual phosphate buffer. Where residual phosphate ions are present at between 3 and 5 mM, for example, pH is difficult to control between 6.0 and 7.0, and some antigens tend to desorb from adjuvants, but the addition of 5 to 10 mM histidine pH and adsorption to be controlled, including during storage at elevated temperatures.

The molar ratio of histidine to free phosphate is preferably at least 1.25:1 e.g. 15:1, 1.75:1, 2:1, 2.25:1, 2.5:1, 3:1, 4:1 etc.

The pH of the composition is preferably between 6 and 7 (e.g. between 6.3 and 7.0). The pH may be maintained by the use of a buffer. This will typically be achieved inherently by the histidine in the composition.

The composition will not, in general, contain: serum (e.g. fetal calf serum etc.) or other such components used in cell culture; host cell DNA at a level of greater than 100 pg/dose for antigens purified from cell culture; living cells.

The composition will generally be sterile and/or pyrogen-free.

The composition may comprise a detergent (e.g. a Tween, such as [Tween 80] *TWEEN™ 80* (*sorbitan monooleate*)) in order to minimise adsorption of antigens to containers.

The composition preferably does not comprise a preservative. Where a preservative is present, mercurial preservatives (e.g. thimerosal) may be used (cf. WO98/34594). Preservatives which may be present or absent are 2-phenoxy-ethanol, methyl parabens, propyl parabens and benzyl alcohol (or mixtures thereof).

Immunogenic Composition and Medicaments

The composition of the invention is typically a vaccine composition.

The invention also provides a composition of the invention for use as a medicament. The medicament is preferably able to raise an immune response in a mammal against the antigen (i.e. it is an immunogenic composition) and is more preferably a vaccine.

The invention also provides the use of a composition of the invention in the manufacture of a medicament for raising an immune response in a mammal against the antigen. The medicament is preferably a vaccine.

The invention also provides a method for raising an immune response in a mammal comprising the step of administering an effective amount of a composition of the invention. The immune response is preferably protective. The method may raise a booster response.

The mammal is preferably a human, and most preferably a child.

These uses and methods are preferably for the prevention and/or treatment of a disease caused by a Neisseria (e.g. meningitis, septicaemia; gonorrhoea etc.), by H. influenzae (e.g. otitis media, bronchitis, pneumonia, cellulitis, pericarditis, meningitis etc.) or by pneumococcus (e.g. meningitis, sepsis, pneumonia etc). The prevention and/or treatment of bacterial meningitis is thus preferred.

Vaccines according to the invention may either be prophylactic (i.e. to prevent infection) or therapeutic (i.e. to treat disease after infection), but will typically be prophylactic.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose (WO00/56365) and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in Remington's Pharmaceutical Sciences [e.g. ref. 88].

Immunogenic compositions used as vaccines comprise an immunologically effective amount of antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine may be administered in conjunction with other immunoregulatory agents.

The vaccine may be administered in conjunction with other immunoregulatory agents.

The vaccine may include an adjuvant in addition to the aluminium salt. Preferred adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in ref. 1), containing 5% Squalene, 0.5% [Tween 80] *TWEEN™ 80* (*sorbitan monooleate*), and 0.5% Span 85 (optionally containing MTP-PE) formulated into submicron particles using a microfluidizer, (b) SAF, containing 10% Squalane, 0.4% [Tween 80] *TWEEN™ 80* (*sorbitan monooleate*), 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% [Tween 80] *TWEEN™ 80* (*sorbitan monooleate*), and one or more bacterial cell wall components from the group consisting of monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3 dMPL) e.g. GB-2220221, EP-A-0689454; (6) combinations of 3 dMPL with, for example, QS21 and/or oil-in-water emulsions e.g. EP-A-0835318, EP-A-0735898, EP-A-0761231; (7) oligonucleotides comprising CpG motifs [Krieg Vaccine 2000, 19, 618-622; Krieg Curr opin Mol Ther 2001 3:15-24; Roman et al., Nat. Med., 1997, 3, 849-854; Weiner et al., PNAS USA, 1997, 94, 10833-10837; Davis et al., J. Immunol., 1998, 160, 870-876; Chu et al., J. Exp. Med., 1997, 186, 1623-1631; Lipford et al., Eur. J. Immunoal., 1997, 27, 2340-2344; Moldoveanu et al., Vaccine, 1988, 16, 1216-1224, Krieg et al., Nature, 1995, 374, 546-549; Klinman et al., PNAS USA, 1996, 93, 2879-2883; Ballas et al., J. Immunol., 1996, 157, 1840-1845; Cowdery et al., J. Immunol., 1996, 156, 4570-4575; Halpern et al., Cell. Immunol., 1996, 167, 72-78; Yamamoto et al., Jpn. J. Cancer Res., 1988, 79, 866-873; Stacey et al., J. Immunol., 1996, 157, 2116-2122; Messina et al., J. Immunol., 1991, 147, 1759-1764; Yi et al., J. Immunol., 1996, 157, 4918-4925; Yi et al., J. Immunol., 1996, 157, 5394-5402; Yi et al., J. Immunol., 1998, 160, 4755-4761; and Yi et al., J. Immunol., 1998, 160, 5898-5906; International patent applications WO96/02555, WO98/16247, WO98/18810, WO98/40100, WO98/55495, WO98/37919 and WO98/52581] i.e. containing at least one CG dinucleotide, with 5-methylcytosine optionally being used in place of cytosine; (8) a polyoxyethylene ether or a polyoxyethylene ester e.g. WO99/52549; (9) a polyoxyethylene sorbitan ester surfactant in combination with an octoxynol (e.g. WO01/21207) or a polyoxyethylene alkyl ether or ester surfactant in combination with at least one additional non-ionic surfactant such as an octoxynol (e.g. WO01/21152); (10) an immunostimulatory oligonucleotide (e.g. a CpG oligonucleotide) and a saponin e.g. WO00/62800; (11) an immunostimulant and a particle of metal salt e.g. WO00/23105; (12) a saponin and an oil-in-water emulsion e.g. WO99/11241; (13) a saponin (e.g. QS21)+3 dMPL+1112 (optionally+a sterol) e.g. WO98/57659; (14) chitosan; (15) cholera toxin or E. coli heat labile toxin, or detoxified mutants thereof [89]; (16) microparticles of poly(α-hydroxy)acids, such as PLG; (17) other substances that act as immunostimulating agents to enhance the efficacy of the composition.

Muramyl peptides include N-acetyl-muramyl-L-threonyl-D-isoglutamine (thr-MDP), N-acetyl-normuramuyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Once formulated, the compositions of the invention can be administered directly to the subject. The subjects to be treated can be animals; in particular, human subjects can be treated. The vaccines are particularly useful for vaccinating children and teenagers.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications (e.g. see WO98/20734), needles, and hyposprays. Dosage treatment may be a single dose schedule or a multiple dose schedule (e.g. including booster doses).

The Step of Admixing Antigen, Aluminium Salt and Histidine

To make compositions of the invention, antigen, aluminium salt and histidine must be combined. It is preferred that, when the antigen and aluminium salt are mixed, the histidine should be present. Histidine is thus present during adsorption to the aluminium salt. This compares with adding histidine to an antigen/aluminium salt combination which already exists i.e. the histidine in the process is not simply added as a buffer after antigen and aluminium salt have interacted, but instead it is present during their interaction.

In the process of the invention, therefore, antigen is preferably admixed with a histidine/aluminium salt mixture. The process of the invention may therefore comprise the following steps: (a) preparing a mixture of the aluminium salt and the histidine; and (b) admixing the antigen with said mixture. The mixture of (a) is preferably aqueous and may be prepared in aqueous conditions or may be a dried mixture which is re-hydrated prior to use.

Once one or more antigens has been adsorbed to an aluminium salt in the presence of histidine, the mixture may be combined with other antigens e.g. combined with existing diphtheria, tetanus, pertussis, polio or hepatitis B virus compositions.

DEFINITIONS

The term "comprising" means "including" as well as "consisting" e.g. a composition "comprising" X may consist exclusively of X or may include something additional e.g. X+Y.

The term "about" in relation to a numerical value x means, for example, x±10%.

MODES FOR CARRYING OUT THE INVENTION

Example 1 pH Stability and Adsorption of Meningococcal B '287' Antigen

Reference 11 discloses a protein antigen named '287' from N. meningitidis serogroup B. Reference 90 discloses a form of this antigen ('ΔG287') which is truncated to remove the N-terminal amino acids up to and including its hexaglycine region. 287 and ΔG287 are both able to elicit a protective immune response in mice. References 16 to 19 disclose OMV antigens from N. meningitidis serogroup B. These OMVs are also able to elicit a protective immune response in mice.

These two antigens were formulated by adsorption to aluminium oxyhydroxide adjuvant. Two adjuvant concentrations (1 mg/ml and 3.3 mg/ml) were tested.

Immunisation studies in mice showed that vaccine immunogenicity is linked to the level of adsorption of the antigens to the adjuvant. To assess adsorption levels, samples of the final formulations were centrifuged at 1300 rpm for 10 minutes and the supernatant was analysed by SDS-PAGE in order to detect the presence of non-adsorbed antigen. The relevant protein standards at an appropriate concentration were loaded adjacent for quantitative comparison.

Figure 1:
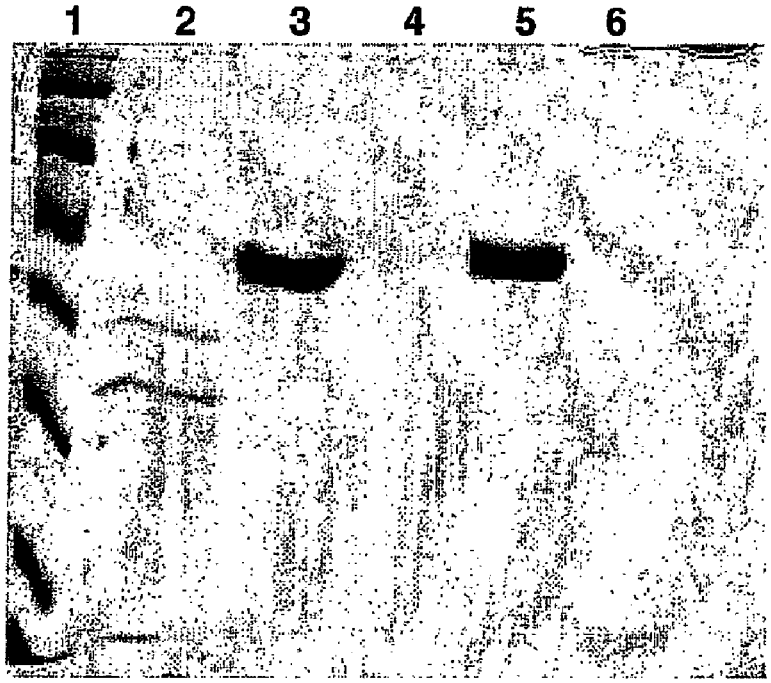
FIG. 1 shows SDS-PAGE analysis of antigenic compositions following centrifugation. Lane 1 includes MW markers (220, 97, 66, 46, 30, 21, 14 kDa). OMV antigen (2 μg) was used in lane 2; ΔG287 antigen was used in lanes 3 (10 μg) and 4 (0.5 μg). The antigen used in lanes 5 and 6 was a combination of OMV (50 μml) and ΔG0287 (100 μg/ml) with 1 mg/ml aluminium oxyhydroxide; the lane 5 composition included 10 mM sodium phosphate (PBS), whereas the lane 6 composition included 5 mM histidine in saline solution.

In order to maintain a stable physiological pH at 4° C. and 37° C. over a period of 4 weeks using sodium phosphate buffer it was found that the composition requires 10 mM sodium phosphate. At this level, however, adsorption of ΔG287 was only 50% (FIG. 1, lane 5). 100% adsorption could be maintained at 2.5 mM sodium phosphate (Lanes 5 of FIGS. 2 & 3), but this composition does not have a stable pH at either 4° C. or 37° C.

It was therefore necessary to find an alternative buffer system which would maintain pH stability without decreasing adsorption.

Figure 2:
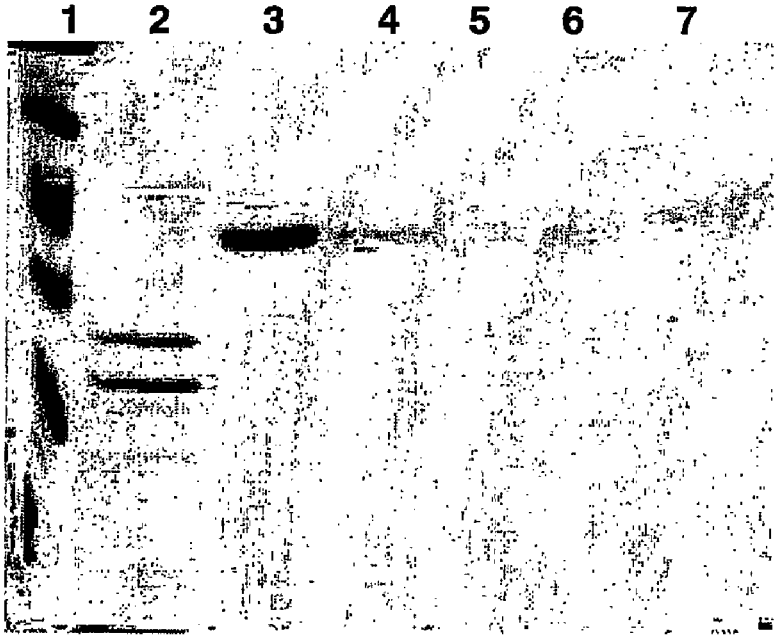
FIG. 2 also shows SDS-PAGE analysis of antigenic compositions following centrifugation. Lane 1 includes the same MW markers as FIG. 1. OMV antigen (2.5 μg) was used in lane 2; ΔG287 antigen was used in lanes 3 (2 μg) and 4 (0.5 μg). The antigen used in lanes 5, 6 and 7 was a combination of OMV (50 μml) and ΔG287 (100 μg/ml) with 1 mg/ml aluminium oxyhydroxide in saline solution (pH 6.5); the lane 5 composition included 2.5 mM sodium phosphate, the lane 6 composition included 5 mM histidine, and the lane 7 composition included 10 mM histidine.
Figure 3:
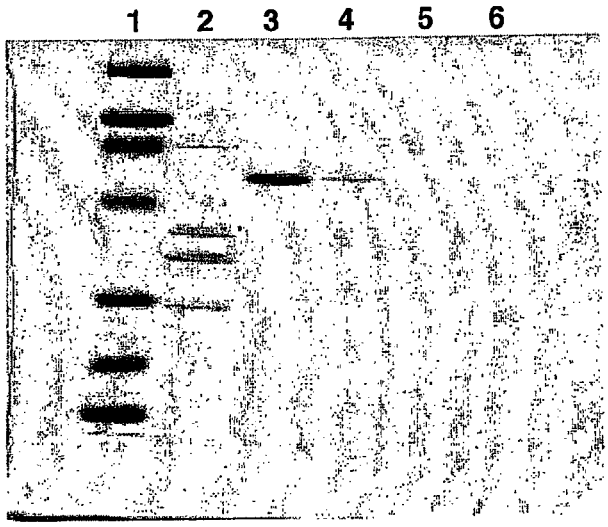
FIG. 3 also shows SDS-PAGE analysis of antigenic compositions following centrifugation. Lane 1 includes the same MW markers as FIG. 1. OMV antigen (2 μg) was used in lane 2; ΔG287 antigen was used in lanes 3 (2 μg) and 4 (0.5 μg). The antigen used in lanes 5 and 6 was a combination of OMV (50 μg/ml) and ΔG287 (100 μg/ml) with 3.3 mg/ml aluminium oxyhydroxide in saline solution (pH 6.5); the lane 5 composition included 2.5 mM sodium phosphate (PBS), whereas the lane 6 composition included 5 mM histidine in saline solution.

Adsorption was 95-100% using 5 mM histidine (Lanes 6 of FIGS. 1, 2 & 3) and also using 10 mM histidine (FIG. 2, lane 7). In terms of adsorption, therefore, 5 mM or 10 mM histidine was equivalent to 2.5 mM sodium phosphate in the presence of either 1 mg/ml (FIGS. 1 & 2) or 3.3 mg/ml (FIG. 3) aluminium oxyhydroxide.

In order to define the pH range in which the vaccine compositions are stable, three starting pH values were chosen (pH 6.0, 6.5 and 7.0) and pH stability was monitored over four weeks in the presence of either 2.5 mM sodium phosphate or 5 mM histidine. Stability was monitored at both 4° C. and 37° C.

The antigen in all vaccines was a combination of ΔG287 (100 μg/ml) and OMV (50 μg/ml) adjuvanted with 3.3 mg/ml aluminium oxyhydroxide.

Figure 4:
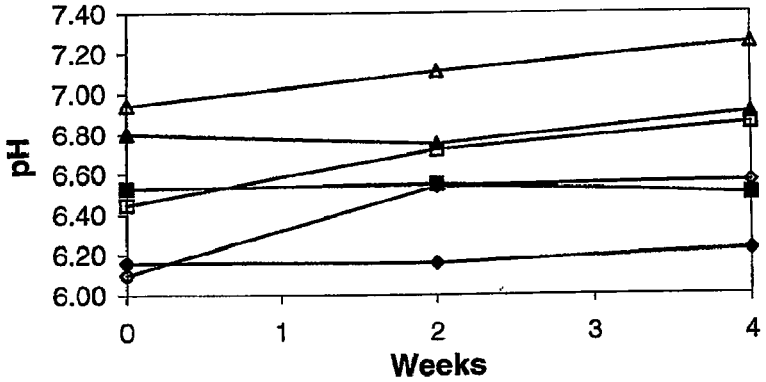
FIG. 4 shows the pH stability of vaccine formulations at 4° C. Filled symbols represent vaccines buffered with 5 mM histidine; open symbols represent vaccines buffered with 25 mM sodium phosphate. The initial pH was 6.0 (diamond), 6.5 (square) or 7.0 (triangle).
Figure 5:
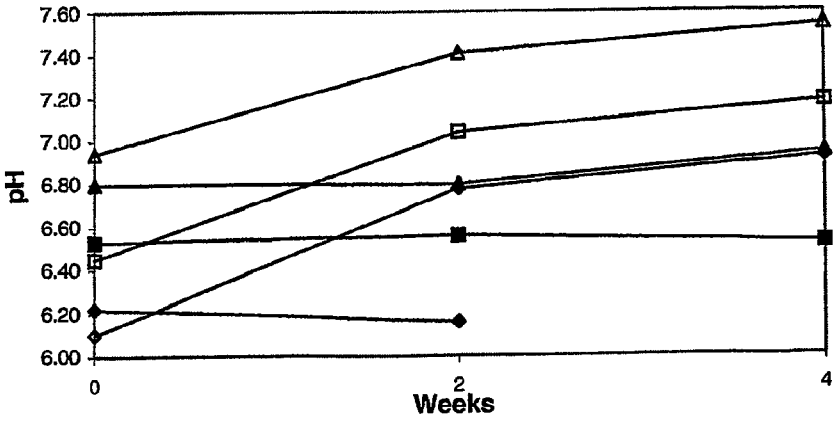
FIG. 5 shows the same at 37° C.

FIG. 4 shows pH stability at 4° C. and FIG. 5 shows pH stability at 37° C. [NB—due to bacterial contamination, no measurement of the pH 6.0 histidine-buffered vaccine was possible at 4 weeks].

At both temperatures the pH tended to increase over time with 2.5 mM sodium phosphate buffer but was stable in the presence of 5 mM histidine buffer.

In comparison with sodium phosphate buffer, therefore, the use of histidine offers pH stability over time without reducing adsorption.

Example 2

Adsorption of Meningococcal C Saccharide Antigen

Saccharide conjugates tend to degrade by hydrolysis [7,8] when present in solution ('liquid' vaccines). Conjugates can be lyophilised to avoid this [7], but this requires adjuvant to be added at the point of reconstitution. It would be preferable to have a liquid form of the vaccine in which the saccharide is not subject to hydrolytic degradation.

This was investigated for a conjugate of meningococcus serogroup C oligosaccharide on $CRM_{197}$ carrier protein [20]. $CRM_{197}$ is acidic and thus does not completely adsorb to negatively charged aluminium phosphates. Histidine, however, is positively charged and it was thought that this might be able to mask the negative charge. Histidine buffer was thus tested with the aim of improving adsorption of MenC-$CRM_{197}$ to aluminium hydroxyphosphate.

Antigen adsorption was evaluated in the presence and absence of histidine buffer by measuring protein concentration in the vaccine supernatant using the BCA protein assay, after centrifugation to separate the adjuvant pellet The vaccines were formulated as 20 μg/ml oligosaccharide and 45 μg/ml $CRM_{197}$ protein. Results were as follows:

| Antigen | Adjuvant | [Histidine] (mM) | Protein (μg/ml) |
|---|---|---|---|
| MenC-$CRM_{197}$ | Hydroxyphosphate | 0 | 42.4 |
| | $Al^{3+}$ = 0.6 mg/ml | 5 | 28.6 |
| | | 10 | 21.7 |

Antigen adsorption thus improves when histidine is present in the formulation: adsorption is about 6% in the absence of histidine; 5 mM histidine increases this to 36%; 10 mM histidine increases adsorption to almost 52%.

Histidine is thus a useful additive for improving the adsorption of antigens to aluminium hydroxyphosphate.

Example 3

Adsorption of Meningococcal B NadA Antigen

NadA (Neisserial adhesin A) from serogroup B N. meningitidis is disclosed as protein '961' in ref. 11 (SEQ IDs 2943 & 2944) and as 'NMB1994' in ref. 13 (see also GenBank accession numbers 11352904 & 7227256). Allelic forms of NadA are disclosed in reference 91. Preferred forms of NadA lack the C-terminus anchor domain ('961c').

Figure 8:
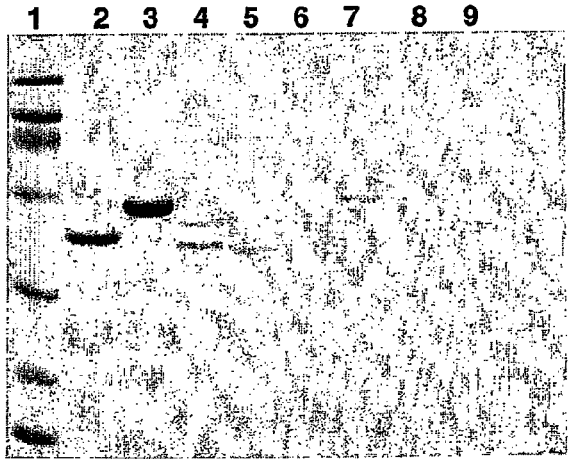
FIG. 8 shows a SDS-PAGE gel for various antigens. Lane 1 contains MW markers. Lanes 2 to 5 contain markers: (2) 961c; (3) 936-741; (4) New Zealand OMVs; and (5) Norwegian OMVs. Lanes 6 to 9 show supernatants of centrifuged histidine formulations of the invention after 1 month storage at 2-8° C.: (6) 961c; (7) 936-741; (8) $OMV_{NZ}$; (9) $OMV_{Norway}$.
Figure 9:
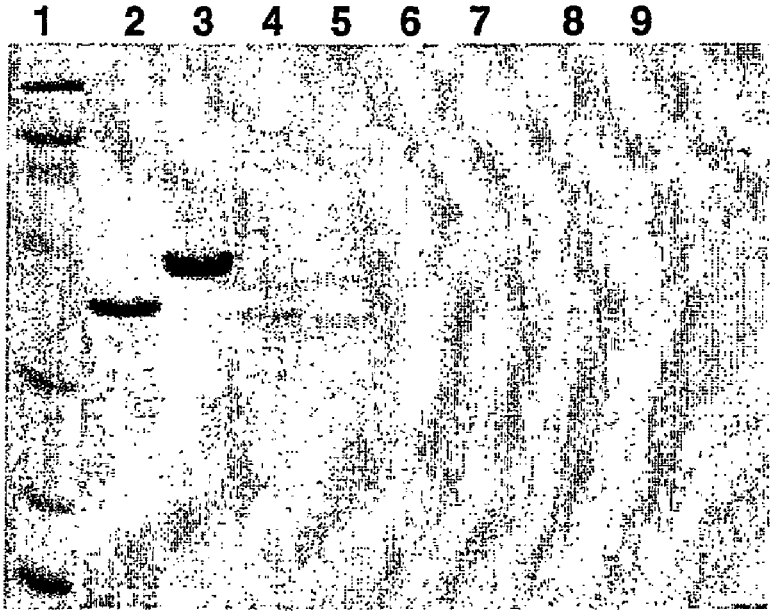
FIG. 9 shows the same as FIG. 8, but lanes 6-9 are after storage at 36-38° C.

961c (100 μg/ml) was adsorbed onto aluminium oxyhydroxide (3 mg/ml) in the presence of 10 mM histidine buffer, pH 65. After 4 weeks of storage at either 2-8° C. or at 36-38° C., the antigen remained 100% adsorbed (FIGS. 8 & 9, lane 6). The pH of the composition was 6.44 at time zero and after 4 weeks of storage rose very slightly to 6.48 (2-8° C.) or 6.47 (36-38° C.).

Example 4

Adsorption of Meningococcal B Hybrid Antigens

Figure 6:
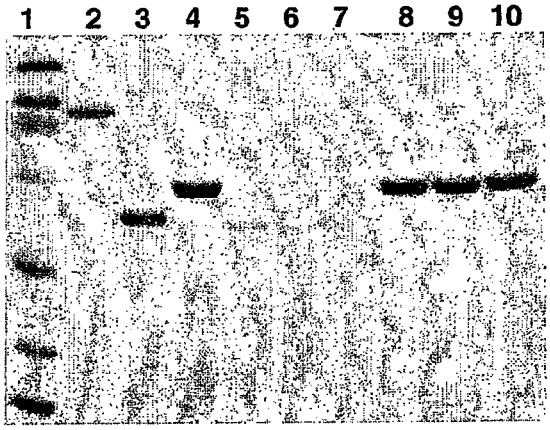
FIG. 6 shows a SDS-PAGE gel for various antigens. Lane 1 contains MW markers. Lanes 2 to 6 contain markers: (2) ΔG287-953; (3) 961c; (4) 936-741; (5) New Zealand OMVs; and (6) Norwegian OMVs. Lanes 7 to 10 show supernatants of centrifuged histidine formulations of the invention after 1 month storage at 2-8° C.: (7) ΔG287-953; (8) 961c+936-741+ΔG287-953; (9) 961c+936-741+ΔG287-953+$OMV_{NZ}$; (10) 961c+936-741+ΔG287-953+$OMV_{Norway}$.
Figure 7:
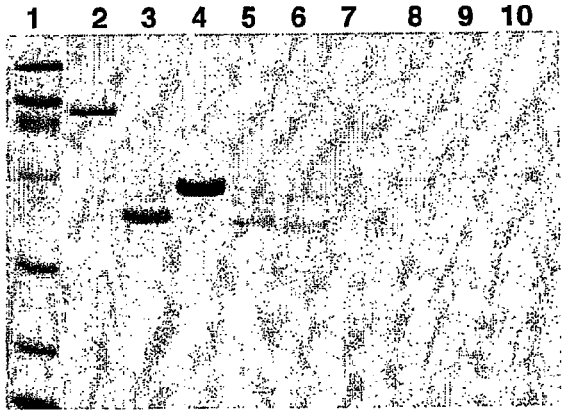
FIG. 7 shows the same as FIG. 6, but lanes 7-10 are after storage at 36-38° C.

References 92 & 93 disclose hybrid expression of meningococcal B antigens. One such hybrid is '$\Delta G287_{nz}$-953' and another is '936-741'. These two hybrids (100 μg/ml) were each adsorbed onto aluminium oxyhydroxide (3 mg/ml) in the presence of 10 mM histidine buffer, pH 6.3. After 4 weeks of storage at either 2-8° C. or at 36-38° C., '$\Delta G287_{nz}$-953' remained 100% adsorbed (FIGS. 6 & 7, lane 7), with pH rising slightly from 6.44 to 6.52 (2-8° C.) or 653 (36-38° C.). '936-741' remained 100% adsorbed at 36-38° C. (FIG. 9, lane 7) but was ~99% adsorbed at 2-8° C. (FIG. 8, lane 7), with pH rising slightly from 6.33 to 6.37 (2-8° C.) or 6.38 (36-38° C.).

Example 5

Adsorption of Meningococcal OMVs

As mentioned above, OMV vaccines from meningococcus B are well known. OMVs were prepared from the Norwegian strain of meningococcus B or from a New Zealand strain (394/98). These two OMV preparations (50 μg/ml) were adsorbed onto aluminium oxyhydroxide (3 mg/ml) in the presence of 10 mM histidine buffer, pH 6.5. After 4 weeks of storage at either 2-8° C. or at 36-38° C., both OMV preparations remained 100% adsorbed (FIGS. 8 & 9, lanes 8 & 9). For the Norwegian OMVs, pH rose slightly from 6.39 to 6.42 over 4 weeks at both storage temperatures. For the New Zealand OMVs, pH rose slightly from 6.40 to 6.42 (2-8° C.) or 6.43 (36-38° C.).

New Zealand OMVs were alternatively formulated with 5 mM histidine. Starting with pure water, the aluminium oxyhydroxide was added, followed by histidine, with 10 minutes mixing. The OMVs were then added and mixed for 15 minutes. NaCl was then added followed by 10 minutes further mixing. The final composition was 3.3 mg/ml aluminium oxyhydroxide, 7.5 mM NaCl, 5 mM histidine, 100 μg/ml OMV, pH 6.42.

During storage at either 2-8° C. or 36-36° C., pH and OMV adsorption varied as follows:

| | pH | | %Adsorption | |
|---|---|---|---|---|
| | 2-8° C. | 36-38° C. | 2-8° C. | 36-38° C. |
| Time zero | 6.42 | 6.42 | 100 | 100 |
| 15 days | 6.36 | 6.37 | 100 | 100 |
| 30 days | 6.35 | 6.34 | 100 | 100 |

Figure 10:
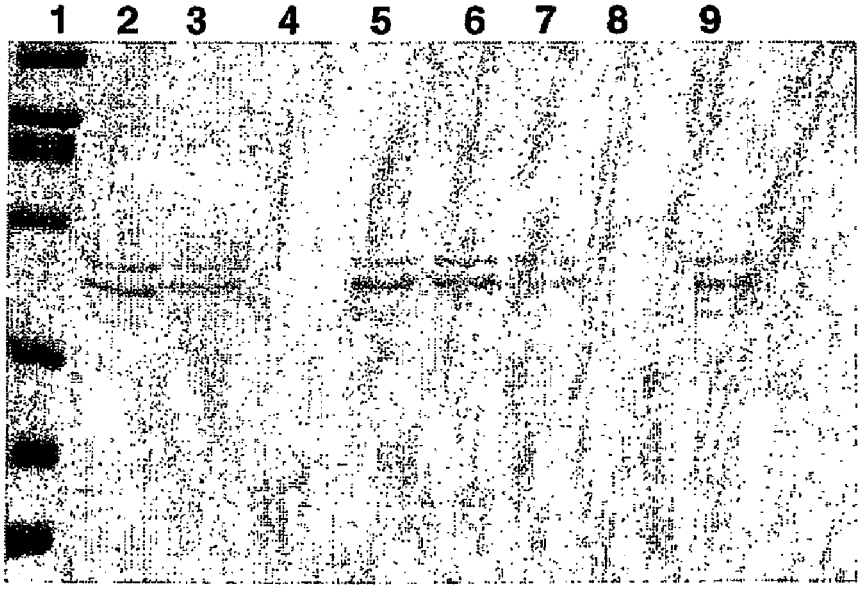
FIG. 10 shows a SDS-PAGE gel for New Zealand OMVs. Lane 1 contains MW markers. Lanes 2, 3, 6 & 7 contain OMV markers stored at either 2-8° C. (lanes 2 & 3) or 36-38° C. (lanes 6 & 7), present at either 2 μg (lanes 2 & 6) or 1 μg (lanes 3 & 7). Lanes 4, 5, 8 & 9 show OMVs in histidine formulations of the invention after 30 days storage at either 2-8° C. (lanes 4 & 5) or 36-38° C. (lanes 8 & 9). Lanes 4 & 8 show supernatant of centrifuged OMVs, whereas lanes 5 & 9 show pellets.

A comparison of lanes 4 & 5 (2-8° C.) or lanes 8 & 9 (36-38° C.) in FIG. 10 shows that OMVs remain adsorbed after 1 month of storage.

Example 6

Adsorption of Mixtures of Meningococcal OMVs and Protein Antigens

961c, $\Delta G287_{nz}$-953 and 936-741 were mixed at 100 μg/ml of each antigen and the mixture was adsorbed onto aluminium oxyhydroxide (3 mg/ml) in the presence of 10 mM histidine buffer, pH 6.3. In two further formulations, OMVs were included (50 μg/ml) from either Norwegian or New Zealand strain meningococcus B.

All antigens in the three mixtures (FIGS. 6 & 7, lanes 8-10) showed 100% adsorption after 4 weeks of storage at either 2-8° C. or at 36-38° C./, except for 936-741 which was ~96% adsorbed in all three mixtures at 2-8° C. and ~99% adsorbed at 36-38° C. The pH of each of the three mixtures rose slightly from 6.53 at time zero to 6.62 after 4 weeks at 2-8° C. At 36-38° C., the pH of three mixtures rose to 6.71±0.02.

The individual antigens brought residual phosphate ions into the mixture from their own PBS. Phosphate ions were sometimes present at between 3 and 5 mM in the combined antigen mixture. In the presence of these high concentrations of residual phosphate buffer, it was difficult to stabilise pH within 6.0 to 7.0, even with 5 mM histidine. When histidine was increased to 10 mM, however, pH was stabilised. Furthermore, the antigens remained adsorbed even after 1 month of storage at either 2-8° C. or at 36-38° C.

Example 7

Adsorption of Meningococcal A Saccharide Antigen

Reference 94 discloses $CRM_{197}$ conjugates of capsular oligosaccharide from serogroup A meningococcus. The conjugates are not fully stable and are therefore prepared in lyophilised form, ready for reconstitution at the time of administration. The lyophilised form was prepared to have components which give the following composition after reconstitution into a unit dose:

| Component | Concentration |
|---|---|
| CRM-MenA | 20 μg saccharide/ml |
| Potassium phosphate buffer | 5 mM |
| Mannitol | 15 mg/ml |

This composition has no adjuvant, so an adjuvant was prepared for its reconstitution:

| Component | Concentration |
|---|---|
| Aluminium oxyhydroxide | 0.68 mg $Al^{3+}$/ml |
| Histidine buffer | 10 mM |
| Sodium chloride | 9 mg/ml |
| [Tween 80]*TWEEN ™ 80* (*sorbitan monooleate*) | 0.005% |
| PH | 7.2 ± 0.05 |

* amorphous hydroxyphosphate, $PO_4$/Al molar ratio between 0.84 and 0.92

Example 8

Adsorption of Meningococcal C, W135 and Y Saccharide Antigens

Reference 94 discloses $CRM_{197}$ conjugates of capsular oligosaccharides from meningococcus serogroups C, W135 and Y. A trivalent mixture of the three conjugates either adsorbed onto an aluminium oxyhydroxide adjuvant (2 mg/ml) or an aluminium hydroxyphosphate adjuvant (0.6 mg/ml $Al^{3+}$) was prepared. The compositions of the two trivalent mixtures were as follows:

| Component | Concentration | Concentration |
|---|---|---|
| Aluminium oxyhydroxide | 0.68 mg $Al^{3+}$/ml | — |
| Aluminium hydroxyphosphate* | — | 0.6 mg $Al^{3+}$/ml |
| CRM-MenC | 20 μg saccharide/ml | 20 μg saccharide/ml |
| CRM-MenY | 20 μg saccharide/ml | 20 μg saccharide/ml |
| CRM-MenW135 | 20 μg saccharide/ml | 20 μg saccharide/ml |
| Sodium phosphate buffer | — | 10 mM |
| Histidine buffer | 10 mM | — |
| Sodium chloride | 9 mg/ml | 9 mg/ml |
| [Tween 80] *TWEEN ™ 80* (*sorbitan monooleate*) | 0.005% | 0.005% |

*amorphous hydroxyphosphate, $PO_4$/Al molar ratio between 0.84 and 0.92

For the oxyhydroxide/histidine formulation, stability of the saccharide components either in the bulk mixture or after packaging into vials was as follows:

| | Stored at 2-8° C. | | Stored at 36-38° C. | |
|---|---|---|---|---|
| Time (days) | Free saccharide (μg/ml) | Free saccharide % | Free saccharide (μg/ml) | Free saccharide % |
| MenC bulk | | | | |
| 0 | <1.2 | <6 | <1.2 | <6 |
| 15 | <1.2 | <6 | <1.2 | <6 |
| 30 | <1.2 | <6 | <1.2 | <6 |
| MenC vials | | | | |
| 0 | <1.2 | <6 | <1.2 | <6 |
| 15 | <1.2 | <6 | <1.2 | <6 |
| 30 | <1.2 | <6 | 1.3 | 6.6 |
| MenW135 bulk | | | | |
| 0 | 2.5 | 12.5 | 2.5 | 12.5 |
| 15 | 2.3 | 11.4 | 3.4 | 16.8 |
| 30 | 2.3 | 11.5 | 3.5 | 17.3 |
| MenW135 vials | | | | |
| 0 | 2.1 | 10.6 | 2.1 | 10.6 |
| 15 | 2.3 | 11.7 | 2.7 | 13.3 |
| 30 | 20. | 10.2 | 3.3 | 16.3 |
| MenY bulk | | | | |
| 0 | 1.7 | 8.3 | 1.7 | 8.3 |
| 15 | <1.3 | <6.3 | 2.0 | 10.2 |
| 30 | 1.3 | 6.3 | 2.4 | 12.2 |
| MenY Vials | | | | |
| 0 | 1.4 | 7.1 | 1.4 | 7.1 |
| 15 | 1.5 | 7.6 | 2.1 | 10.7 |
| 30 | 1.3 | 6.3 | 2.9 | 14.3 |

Free saccharide levels are thus stable for at least 1 month at 2-8° C., before and after packaging.

Under thermal stress conditions, small increases in free saccharide are seen over time for MenW135 and MenY, but MenC remains stable.

Over the 30 days, pH in vials and bulk was stable at 7.15±0.05 at both storage temperatures.

Example 9

Adsorption of Meningococcal A, C, W135 and Y Saccharide Antigens

The two trivalent liquid compositions of example 8 were diluted and 0.5 ml used to reconstitute the lyophilised MenA conjugate of example 7. The resulting tetravalent mixture was administered to ten Balb/c mice (female 68 weeks old) per group by subcutaneous injection at day 0 and 28. The mixture contained 2 μg of each saccharide conjugate per dose, which represents ⅕ of the single human dose (SHD). Controls were saline or unconjugated homologous polysaccharides. Bleedings were performed before immunization and then at day 42, with sera stored at −70° C.

All the conjugates used were safe and immunogenic in the animals. GMT post-II ELISA titres (with 95% confidence intervals) were as follows:

| Vaccine | Adjuvant | A | Y | W135 | C |
|---|---|---|---|---|---|
| MenA (lyophilised and resuspended) | Hydroxyphosphate | 172 (69-439) | — | — | — |
| | Oxyhydroxide | 619 (419-906) | — | — | — |
| MenY | Hydroxyphosphate | — | 328 (147-731) | | |
| | Oxyhydroxide | — | 452 (344-593) | — | — |
| MenW | Hydroxyphosphate | — | — | 80 (28-225) | — |
| | Oxyhydroxide | — | — | 277 (185-411) | — |
| MenC | Hydroxyphosphate | — | — | — | 317 (152-659) |
| | Oxyhydroxide | — | — | — | 723 (615-851) |
| MenA (lyophilized) + MenC, W135, Y | Hydroxyphosphate | 32 (15-68) | 397 (252-627) | 99 (35-288) | 114 (53-246) |
| | Oxyhydroxide | 206 (112-372) | 141 (97-205) | 139 (76-251) | 163 (122-218) |

Typically, therefore, titres are higher in the aluminium oxyhydroxide+histidine groups. Serum bactericidal titres were also generally better in the aluminium oxyhydroxide+histidine groups.

In parallel experiments, mice were immunised as described above but the vaccine compositions contained different ratios of the various oligosaccharide conjugates. Lyophilised MenA oligo-conjugate was used in all experiments. ELISA titres were as follows:

| Antigen quantity (ug/dose) | | | | Aluminium | GMT ELISA (95% confidence interval) | | | |
|---|---|---|---|---|---|---|---|---|
| A | C | W135 | Y | adjuvant | A | C | W135 | Y |
| 4 | 2 | 2 | 2 | Hydroxyphosphate | 177 (107-291) | 367 (263-510) | 239 (135-424) | 239 (184-311) |
| 4 | 2 | 2 | 2 | Oxyhydroxide | 390 (313-486) | 494 (345-706) | 338 (266-430) | 158 (96-260) |
| 2 | 2 | 2 | 2 | Hydroxyphosphate | 132 (59-296) | 582 (268-1155) | 143 (75-272) | 247 (152-400) |
| 2 | 2 | 2 | 2 | Oxyhydroxide | 337 (239-476) | 569 (462-679) | 171 (117-251) | 100 (59-169) |

A second set of experiments was performed using a dosage of 2 μg/ml saccharide for MenA and MenC, half that dosage for MenY, and a quarter dosage for MenW135. ELISA titres were as follows:

| Antigen quantity (ug/dose) | | | | Aluminium | GMT ELISA (95% confidence interval) | | | |
|---|---|---|---|---|---|---|---|---|
| A | C | W135 | Y | adjuvant | A | C | W135 | Y |
| 2 | 2 | 2 | 2 | Hydroxyphosphate | 32 (15-68) | 114 (53-246) | 99 (35-288) | 397 (252-627) |
| | | | | Oxyhydroxide | 206 (112-372) | 163 (122-218) | 139 (76-251) | 141 (97-205) |
| 2 | 2 | 1 | 0.5 | Hydroxyphosphate | 96 (49-187) | 238 (101-561) | 42 (20-89) | 315 (114-867) |
| | | | | Oxyhydroxide | 293 (144-597) | 267 (158-451) | 83 (43-163) | 244 (152-392) |

At least for serogroups A, C and W135, therefore, the oxyhydroxide+histidine formulation generally gives better titres than hydroxyphosphate at these different antigen ratios.

It will be understood that the invention has been described by way of example only and modifications may be made whilst remaining within the scope and spirit of the invention.

REFERENCES

The Contents of which are Hereby Incorporated by Reference

1—Vaccine Design: subunit & adjuvant approach (1995) Powell & Newman (ISBN: 030644867X)
2—International patent application WO93/24148.
3—International patent application WO97/00697.
4—International patent application WO98/48525.
5—Burrell et al. (2000) Vaccine 18:2188-2192.
6—Burrell et al. (1999) Vaccine 17:2599-2603.
7—Corbel (1996) Dev Biol Stand 87:113-124.
8—Sturgess et al. (1999) Vaccine 17:1169-1178.
9—International patent application WO99/24578.
10—International patent application WO99/36544.
11—International patent application WO99/57280.
12—International patent application WO00/22430.
13—Tettelin et al. (2000) Science 287:1809-1815.
14—International patent application WO96/29412.
15—Pizza et al. (2000) Science 287:1816-1820.
16—International patent application WO01/52885.
17—Bjune et al. (1991) Lancet 338(8775):1093-1096.
18—Fukasawa et al. (1999) Vaccine 17:2951-2958.
19—Rosenqvist et al. (1998) Dev. Biol. Stand. 92:323-333.
20—Costantino et al. (1992) Vaccine 10:691-698.
21—Costantino et al. (1999) Vaccine 17:1251-1263.
22—Watson (2000) Pediatr Infect Dis J 19:331-332.
23—Rubin (2000) Pediar Clin North Am 47:269-285, v.
24—Jedrzejas (2001) Microbiol Mol Biol Rev 65:187-207.
25—Gustafsson et al. (1996) N. Engl. J. Med. 334:349-355.
26—Rappuoli et al. (1991) TIBTECH 9:232-238.
27—Vaccines (1988) eds. Plotlin & Mortimer. ISBN 0-7216-19460.
28—Del Guidice et al. (1998) Molecular Aspects of Medicine 19:1-70.
29—International patent application WO93/18150.
30—International patent application WO99/53310.
31—International patent application WO98/04702.
32—International patent application WO02/02606.
33—Kalman et al. (1999) Nature Genetics 21:385-389.
34—Read et al. (2000) Nucleic Acids Res 28:1397-406.
35—Shirai et al (2000) J. Infect. Dis. 181(Suppl 3):S524-S527.
36—International patent application WO99/27105.
37—International patent application WO00/27994.
38—International patent application WO00/37494.
39—International patent application WO99/28475.
40—Ross et al. (2001) Vaccine 19:4135-4142.
41—McMichael (2000) Vaccine 19 Suppl 1:S101-107.
42—Schuchat (1999) Lancet 353(9146):51-6.
43—International patent application WO02/34771.
44—Dale (1999) Infect Dis Clin North Am 13:227-43, viii.
45—Ferretti et al. (2001) PNAS USA 98: 4658-4663.
46—Kuroda et al. (2001) Lancet 357(9264):1225-1240; see also pages 1218-1219.
47—J Toxicol Clin Toxicol (2001) 39:85-100.
48—Demicheli et al. (1998) Vaccine 16:880-884.
49—Stepanov et al. (1996) J Biotechnol 44:155-160.
50—Bell (2000) Pediatr Infect Dis J 19:1187-1188.
51—Iwarson (1995) APMIS 103:321-326.
52—Gerlich et al. (1990) Vaccine 8 Suppl:S63-68 & 79-80.
53—Hsu et al. (1999) Clin Liver Dis 3:901-915.
54—Sutter et al. (2000) Pediatr Clin North Am 47:287-308.
55—Zimmerman & Spann (1999) Am Fam Physician 59:113-118, 125-126.
56—Dreesen (1997) Vaccine 15 Suppl:S2-6.
57—MMWR Morb Mortal Wkly Rep 1998 Jan. 16; 47(1):12, 19.
58—Ingram (2001) Trends Neurosci 24:305-307.
59—Rosenberg (2001) Nature 411:380-384.
60—Moingeon (2001) Vaccine 19:1305-1326.
61—Ramsay et al. (2001) Lancet 357(9251):195-196.
62—Lindberg (1999) Vaccine 17 Suppl 2:S28-36.
63—Buttery & Moxon (2000) J R Coll Physicians Lond 34:163-168.
64—Ahmad & Chapnick (1999) Infect Dis Clin North Am 13:113-133, vii.
65—Goldblatt (1998) J. Med. Microbiol. 47:563-567.
66—European patent 0 477 508.
67—U.S. Pat. No. 5,306,492.
68—International patent application WO98/42721.
69—Conjugate Vaccines (eds. Cruse et al.) ISBN 3805549326, particularly vol. 10:48-114.
70—Hermanson (1996) Bioconjugate Techniques ISBN: 01-23423368 or 012342335X.
71—European patent application 0372501.
72—European patent application 0378881.
73—European patent application 0427347.
74—International patent application WO93/17712.
75—International patent application WO98/58668.
76—European patent application 0471177.
77—International patent application WO00/56360.
78—International patent application WO00/61761.
79—Robinson & Tones (1997) Seminars in Immunology 9:271-283.
80—Donnelly et al. (1997) Annu Rev Immunol 15:617-648.
81—Scott-Taylor & Dalgleish (2000) Expert Opin Investig Drugs 9:471-480.
82—Apostolopoulos & Plebanski (2000) Curr Opin Mol Ther 2:441-447.
83—Ilan (1999) Curr Opin Mol Ther 1:116-120.
84—Dubensky et al. (2000) Mol Med 6:723-732.
85—Robinson & Pertmer (2000) Adv Virus Res 55:1-74.
86—Donnelly et al. (2000) Am J Respir Crit Care Med 162(4 Pt 2):5190-193.
87—Davis (1999) Mt Sinai J Med 66:84-90.
88—Gennaro (2000) Remington: The Science and Practice of Pharmacy. 20th edition, ISBN: 0683306472.
89—WO93/13202.
90—International patent application WO01/64922.
91—International patent application filed 26 Jul. 2002 under attorney reference P027797WO in the name of CHIRON SpA claiming priority from UK patent applications 0118401.9, 0121591.2 and 0211025.2.
92—International patent application WO01/64920.
93—UK patent application 0121591.2.
94—International patent application filed 20 Jun. 2002 under attorney reference P027504WO in the name of CHIRON SpA claiming priority from UK patent application 0115176.0.

What is claimed is:

1. A composition comprising [an antigen] *a mixture comprising one or more antigens selected from the group consisting of an outer-membrane vesicle (OMV) preparation from N. meningitidis and a saccharide antigen from N. meningitidis*, an aluminium salt, and histidine, [said composition further comprising at least about 2.5 mM of free phosphate] *wherein the one or more antigens are adsorbed to the aluminium salt, wherein the composition does not comprise an antigen from B. pertussis, and wherein the histidine has a concentration from about 1 mM to about 100 mM.*

2. The composition of claim 1 comprising from about 2.5 to about 5 mM of free phosphate.

3. The composition of claim 1, wherein *one of* the [antigen] *one or more antigens* is [a protein antigen or] a saccharide antigen.

4. The composition of claim 3, wherein the saccharide antigen is a conjugated oligosaccharide antigen.

5. The composition of claim 1, wherein the antigen is a bacterial antigen selected from the group consisting of:

a protein antigen from N. meningitidis;
an outer-membrane vesicle (OMV) preparation from N. meningitidis;
a saccharide antigen from N. meningitidis;
a saccharide antigen from Streptococcus pnemnoniae;
[an antigen from Bordetella pertussis;]
a diphtheria antigen;
a tetanus antigen;
a protein antigen from Helicobacter pylori;
a saccharide antigen from Haemophilus influenzae;
an antigen from N. gonorrhoeae;
an antigen from Chlamydia pneumoniae;
an antigen from Chlamydia trachomatis;
an antigen from Porphyromonas gingivalis;
an antigen from Moraxella catarrhalis;
an antigen from Streptococcus agalactiae;
an antigen from Streptococcus pyogenes; and
an antigen from Staphylococcus aureus.

6. The composition of claim 5, wherein *one of* the [antigen] *one or more antigens* is [a protein antigen from N. meningitides serogroup B or] a saccharide antigen from N. meningitides serogroup C.

7. The composition of claim 1, wherein *one of* the [antigen] *one or more antigens* is selected from the group consisting of [a protein antigen from N. meningitidis serogroup B;] a saccharide antigen from N. meningitidis serogroup A, C, W135 or Y[; a diphtheria antigen; a tetanus antigen; and an antigen from hepatitis B virus].

[8. The composition of claim 7, wherein the antigen is the protein antigen ΔG287 from N. meningitidis serogroup B or the diphtheria toxoid antigen $CRM_{197}$ mutant.]

[9. The composition of claim 1, wherein the antigen is adsorbed onto the aluminum salt.]

10. The composition of claim [9] *1*, wherein the aluminium salt is selected from the group consisting of an aluminum hydroxide salt, an aluminum phosphate salt, and mixtures thereof.

11. The composition of claim 10, wherein the aluminium salt is selected from the group consisting of aluminum oxyhydroxide, aluminum hydroxyphosphate, and mixtures thereof.

12. The composition of claim 11, wherein aluminium salt is aluminium hydroxyphosphate and the antigen is an acidic antigen.

[13. The composition of claim 1, wherein the histidine has a concentration from about 1 mM to about 250 mM.]

[14. The composition of claim 13, wherein the histidine has a concentration from about 1 mM to about 100 mM.]

15. The composition of claim [14] *1*, wherein the histidine has a concentration from about 1 mM to about 10 mM.

16. The composition of claim 15, wherein the histidine has a concentration from about 5 mM to about 10 mM.

17. The composition of claim 1, further comprising a sodium salt.

18. The composition of claim 17, wherein the sodium salt is sodium phosphate.

19. The composition of claim 17, wherein the sodium salt has a concentration from about 2.5 mM to about 5 mM.

20. The composition of claim 1, wherein the composition has a pH between 6 and 7.

21. The composition of claim 1, further comprising a pharmaceutically acceptable carrier.

22. The composition of claim 1, comprising more than one antigen.

23. The composition of claim 22, wherein more than one of the antigens is adsorbed onto [an] *the* aluminum salt.

24. The composition of claim 23, comprising 2, 3, 4, 5, 6, 7 or 8 antigens selected from the following antigens: a protein antigen from N. meningitidis serogroup B; [an antigen from Bordetella pertussis;] a diphtheria antigen; a tetanus antigen; an antigen from hepatitis B virus; a saccharide antigen from Haemophilus influenzae; inactivated polio virus; and a saccharide antigen from N. meningitidis serogroup C.

25. A method for raising an immune response in a mammal comprising the step of administering an effective amount of the composition of claim 1.

26. The method of claim 25, wherein the mammal is a human.

27. The method of claim 25, wherein the composition comprises from about 2.5 mM to about 5 mM of free phosphate.

28. The method of claim 25, wherein the composition comprises histidine in a concentration from about 1 mM to about 250 mM.

29. The method of claim 28, wherein the composition comprises histidine in a concentration from about 1 mM to about 100 mM.

30. The method of claim 29, wherein the composition comprises histidine in a concentration from about 1 mM to about 10 mM.

31. The method of claim 30, wherein the composition comprises histidine in a concentration from about 5 mM to about 10 mM.

32. A process for producing the antigenic composition of claim 1, the process comprising [admixing the antigen, the aluminium salt, and histidine, wherein histidine is present during adsorption of the antigen to the aluminum salt] *, a first step of admixing (i) the aluminium salt and (ii) histidine, to give a histidine/aluminium salt admixture; and a second step of admixing (i) said histidine/aluminium salt admixture and (ii) the antigen, wherein the antigen is adsorbed to the aluminium salt.*

[33. The process of claim 32, wherein the admixing comprises: a first step of admixing (i) the aluminium salt and (ii) histidine, to give a histidine/aluminium salt admixture; and a second step of admixing (i) said histidine/aluminium salt admixture and (ii) one or more antigens.]

34. The process of claim 32, further comprising combining the antigenic composition with another antigenic composition.

35. The process of claim 32, wherein the antigenic composition comprises from about 2.5 mM to about 5 mM of free phosphate.

36. The process of claim 32, wherein the antigenic composition comprises from about 1 mM to about 250 mM of histidine.

37. The process of claim 36, wherein the antigenic composition comprises from about 1 mM to about 100 mM of histidine.

38. The process of claim 37, wherein the antigenic composition comprises from about 1 mM to about 10 mM of histidine.

39. The process of claim 38, wherein the antigenic composition comprises from about 5 mM to about 10 mM of histidine.

40. A vaccine comprising the composition of claim 1 and a pharmaceutically acceptable carrier or excipient.

41. The vaccine of claim 40, comprising from about 2.5 mM to about 5 mM of free phosphate.

[42. The vaccine of claim 40, comprising from about 1 mM to about 250 mM of histidine.]

[43. The vaccine of claim 42, comprising from about 1 mM to about 100 mM of histidine.]

44. The vaccine of claim [43] *40*, comprising from about 1 mM to about 10 mM of histidine.

45. The vaccine of claim 44, comprising from about 5 mM to about 10 mM of histidine.

46. The method of claim 25, wherein the composition comprises a mixture of antigens, essentially a single aluminium salt, histidine, and at least about 2.5 mM of free phosphate, wherein said single aluminum salt is present in a ratio of at least 100:1 relative to any other aluminum salt in the composition.

47. The method of claim 46, wherein the composition comprises from about 2.5 mM to about 5 mM of free phosphate.

48. The method of claim 46, wherein the composition comprises histidine in a concentration from about 1 mM to about 250 mM.

49. The method of claim 48, wherein the composition comprises histidine in a concentration from about 1 mM to about 100 mM.

50. The method of claim 49, wherein the composition comprises histidine in a concentration from about 1 mM to about 10 mM.

51. The method of claim 50, wherein the composition comprises histidine in a concentration from about 5 mM to about 10 mM.

52. The method of claim 46, wherein the single aluminum salt is an aluminum hydroxide or an aluminum phosphate.

53. The method of claim 52, wherein the single aluminum salt is aluminum oxyhydroxide or aluminum hydroxyphosphate.

*54. A composition comprising a mixture comprising one or more antigens selected from the group consisting of an outer-membrane vesicle (OMV) preparation from N. meningitidis and a saccharide antigen from N. meningitidis, an aluminium salt, a sodium salt, and histidine, wherein the one or more antigens are adsorbed to the aluminium salt, and wherein the composition does not comprise an antigen from B. pertussis.*

*55. A composition comprising a mixture comprising one or more protein antigens from N. meningitidis, an aluminium salt, and histidine, wherein the one or more antigens are adsorbed to the aluminium salt, and wherein the composition does not comprise an antigen from B. pertussis.*

*56. A composition comprising a mixture comprising one or more antigens selected from the group consisting of a protein antigen from N. meningitidis; an outer-membrane vesicle (OMV) preparation from N. meningitidis and a saccharide antigen from N. meningitidis, an aluminium phosphate salt, and histidine, wherein the one or more antigens are adsorbed to the aluminium phosphate salt, and wherein the composition does not comprise an antigen from B. pertussis.*

*57. The composition of any one of claims 54-56, wherein the histidine has a concentration from about 1 mM to about 100 mM.*

*58. The composition of claim 57, wherein the histidine has a concentration from about 1 mM to about 10 mM.*

*59. The composition of claim 58, wherein the histidine has a concentration from about 5 mM to about 10 mM.*

*60. The composition of any one of claims 1, 54, and 56, wherein the one or more antigens are protein antigens from N. meningitidis.*

*61. The composition of any one of claims 1, 54, and 55, wherein the aluminium salt is an aluminum phosphate salt.*

*62. The composition of any one of claims 1, 55, and 56, further comprising a sodium salt.*

*63. A formulation which stabilizes a N. meningitidis 741 protein composition, the formulation comprising (i) a pH buffered solution comprising histidine (ii) a detergent, and (iii) a N. meningitidis 741 protein.*

*64. A composition comprising a mixture comprising one or more protein antigens from N. meningitidis, an aluminium salt, and histidine, wherein the composition does not comprise an H. influenzae saccharide antigen.*

*65. The composition of any one of claims 54-56, wherein the histidine has a concentration from about 1 mM to about 100 mM.*

*66. A composition comprising a mixture comprising one or more protein antigens from N. menigitidis, an aluminium salt, and histidine, wherein the one or more protein antigens are adsorbed to the aluminium salt and wherein the histidine has a concentration from about 1 mM to about 100 mM.*

*67. The composition of claim 66 comprising from about 2.5 to about 5 mM of free phosphate.*

*68. The composition of claim 66, wherein one of the one or more protein antigens is ΔG287 from N. meningitidis serogroup B.*

*69. The composition of claim 66, wherein the aluminium salt is selected from the group consisting of an aluminium hydroxide salt, an aluminium phosphate salt, and mixtures thereof.*

*70. The composition of claim 66, wherein the aluminium salt is selected from the group consisting of aluminium oxyhydroxide, aluminium hydroxyphosphate, and mixtures thereof.*

*71. The composition of claim 66, wherein aluminium salt is aluminium hydroxyphosphate and the antigen is an acidic antigen.*

*72. The composition of claim 66, wherein the histidine has a concentration from about 1 mM to about 10 mM.*

*73. The composition of claim 72, wherein the histidine has a concentration from about 5 mM to about 10 mM.*

*74. The composition of claim 66, further comprising a sodium salt.*

*75. The composition of claim 66, wherein the composition has a pH between 6 and 7.*

*76. The composition of claim 66, further comprising a pharmaceutically acceptable carrier.*

*77. The composition of claim 66, comprising two protein antigens from N. meningitidis.*

*78. A method for raising an immune response in a mammal comprising the step of administering an effective amount of the composition of claim 66.*

*79. The method of claim 78, wherein the mammal is a human.*

*80. The method of claim 78, wherein the composition comprises from about 2.5 mM to about 5 mM of free phosphate.*

*81. The method of claim 78, wherein the composition comprises histidine in a concentration from about 1 mM to about 10 mM.*

*82. The method of claim 81, wherein the composition comprises histidine in a concentration from about 5 mM to about 10 mM.*

*83. A process for producing the antigenic composition of claim 66, the process comprising, a first step of admixing (i) the aluminium salt and (ii) histidine, to give a histidine/*

*aluminium salt admixture; and a second step of admixing (i) said histidine/aluminium salt admixture and (ii) the antigen, wherein the antigen is adsorbed to the aluminium salt.*

*84. The process of claim 83, further comprising combining the antigenic composition with another antigenic composition.*

*85. The process of claim 83, wherein the antigenic composition comprises from about 2.5 mM to about 5 mM of free phosphate.*

*86. The process of claim 83, wherein the antigenic composition comprises from about 1 mM to about 10 mM of histidine.*

*87. The process of claim 86, wherein the antigenic composition comprises from about 5 mM to about 10 mM of histidine.*

*88. A vaccine comprising the composition of claim 66 and a pharmaceutically acceptable carrier or excipient.*

*89. The vaccine of claim 88, comprising from about 2.5 mM to about 5 mM of free phosphate.*

*90. The vaccine of claim 88, comprising from about 1 mM to about 10 mM of histidine.*

*91. The vaccine of claim 90, comprising from about 5 mM to about 10 mM of histidine.*

*92. The composition of any one of claims 54-56 and 66, wherein the $Al^{+++}$ has a concentration of at least 10 μg/mL.*

*93. The composition of any one of claims 54-56 and 66, wherein the one or more antigens are present at a concentration of at least 1 μg/mL.*

*94. The composition of any one of claims 54-56 and 66, wherein the composition comprises no viral antigens.*

*95. The composition of any one of claims 54-56 and 66, wherein the composition comprises a sodium chloride salt.*

*96. The composition of any one of claims 54-56 and 66, wherein the composition does not comprise a preservative.*

*97. The composition of any one of claims 54-56 and 66, wherein the composition does not comprise an H. influenzae saccharide antigen.*

*98. The composition of any one of claims 54-56 and 66, wherein one of the one or more antigens is the protein antigen 741 from N. meningitidis serogroup B.*

*99. A process for producing the antigenic composition of claim 55, the process comprising, a first step of admixing (i) the aluminium salt and (ii) histidine, to give a histidine/aluminium salt admixture; and a second step of admixing (i) said histidine/aluminium salt admixture and (ii) the protein antigen from N. meningitidis serogroup B, wherein the protein antigen from N. meningitidis serogroup B is adsorbed to the aluminium salt.*

*100. The process of claim 99, further comprising combining the antigenic composition with another antigenic composition.*

*101. The process of claim 99, wherein the antigenic composition comprises from about 5 mM to about 10 mM of histidine.*

*102. A vaccine comprising the composition of claim 55 and a pharmaceutically acceptable carrier or excipient.*

*103. The vaccine of claim 102, comprising from about 5 mM to about 10 mM of histidine.*

*104. The composition of claim 55, wherein the aluminium phosphate salt is the only aluminium salt in the composition.*

*105. The composition of claim 64, wherein the aluminium salt is an aluminium phosphate salt, and the aluminium phosphate salt is the only aluminium salt in the composition.*

*106. The composition of claim 64, wherein the composition does not comprise not comprise an antigen from B. pertussis.*

*107. A composition comprising a mixture comprising two protein antigens from N. meningitidis, an aluminium hydroxyphosphate salt, histidine, and a sodium chloride salt, wherein the two protein antigens are adsorbed to the aluminium hydroxyphosphate salt, wherein the histidine has a concentration from about 5 mM to about 10 mM L-histidine, wherein the composition has a pH between 6 and 7, wherein the $Al^{+++}$ of the alumninium hydroxyphosphate has a concentration of at least 10 μg/mL, wherein the two protein antigens are each present at a concentration of at least 1 μg/mL, wherein the composition comprises no viral antigens, wherein the composition does not comprise a preservative, and wherein the composition does not comprise an H. influenzae saccharide antigen or an antigen from B. pertussis.*

* * * * *